(12) United States Patent
Garti et al.

(10) Patent No.: US 10,568,834 B2
(45) Date of Patent: Feb. 25, 2020

(54) DELIVERY SYSTEMS FOR PROPOFOL

(71) Applicant: Yissum Research Development Company of the Hebrew University of Jerusalem Ltd., Jerusalem (IL)

(72) Inventors: Nissim Garti, Ramat HaSharon (IL); Sharon Garti Levi, Modi'in (IL); Abraham Aserin, Jerusalem (IL); My Perlstein, Hod-Hasharon (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 15/741,005

(22) PCT Filed: Jun. 29, 2016

(86) PCT No.: PCT/IL2016/050696
§ 371 (c)(1),
(2) Date: Dec. 29, 2017

(87) PCT Pub. No.: WO2017/002117
PCT Pub. Date: Jan. 5, 2017

(65) Prior Publication Data
US 2019/0008770 A1    Jan. 10, 2019

Related U.S. Application Data

(60) Provisional application No. 62/187,309, filed on Jul. 1, 2015.

(51) Int. Cl.
| | | |
|---|---|---|
| *A61K 9/107* | (2006.01) | |
| *A61K 9/00* | (2006.01) | |
| *A61K 47/10* | (2017.01) | |
| *A61K 47/14* | (2017.01) | |
| *A61K 47/26* | (2006.01) | |
| *A61K 31/05* | (2006.01) | |
| *A61K 47/42* | (2017.01) | |
| *A61P 23/02* | (2006.01) | |

(52) U.S. Cl.
CPC .......... *A61K 9/1075* (2013.01); *A61K 9/0019* (2013.01); *A61K 31/05* (2013.01); *A61K 47/10* (2013.01); *A61K 47/14* (2013.01); *A61K 47/26* (2013.01); *A61K 47/42* (2013.01); *A61P 23/02* (2018.01)

(58) Field of Classification Search
CPC .... A61K 9/1075; A61K 9/0019; A61K 47/10; A61K 47/14; A61K 47/26; A61K 31/05; A61K 47/42; A61P 23/02
See application file for complete search history.

(56) References Cited

U.S. PATENT DOCUMENTS

| | | | |
|---|---|---|---|
| 2002/0022667 A1* | 2/2002 | Pace | A61K 9/0019 514/731 |
| 2005/0004234 A1 | 1/2005 | Bell et al. | |
| 2010/0041769 A1 | 2/2010 | Pacheco et al. | |
| 2010/0160456 A1 | 6/2010 | Quiroga | |

FOREIGN PATENT DOCUMENTS

| | | | |
|---|---|---|---|
| IN | 28/2010 | | 7/2010 |
| KR | 10-2001-0055736 A | | 7/2001 |
| KR | 2001055736 | * | 7/2001 |
| RU | 2 535 001 C1 | | 12/2014 |
| WO | 00/78301 A1 | | 12/2000 |
| WO | 03/105607 A1 | | 12/2003 |
| WO | 2005/079758 A1 | | 9/2005 |
| WO | 2007/006334 A1 | | 1/2007 |
| WO | 2007/123790 A1 | | 11/2007 |
| WO | 2008/049178 A1 | | 5/2008 |
| WO | 2008/058366 A1 | | 5/2008 |

OTHER PUBLICATIONS

Gupta et al. (J. of Pharmaceutical Sci, 97(1), (2008).*
Baker et al. (Anes. 2005, 103; 860-870.*
Cai et al., "A propofol microemulsion with low free propofol in the aqueous phase: Formulation, physicochemical characterization, stability and pharmacokinetics", International Journal of Pharmaceutics, 436 (2012) 536-544.
Cho et al., "Formulation and Evaluation of an Alternative Triglyceride-free Propofol Microemulsion", Arch Pharm Res, vol. 33, No. 9, pp. 1375-1387, (2010).
Davis, "19: The stability of fat emulsions for intravenous administration", Advances in Clinical Nutrition, pp. 213-239, (1983).
Garti et al., "Nano-sized self-assemblies of nonionic surfactants as solubilization reservoirs and microreactors for food systems", Soft Matter, 2005, 1, 206-218.
Li et al., "Preparation and evaluation of novel mixed micelles as nanocamers for intravenous delivery of propofol", Nanoscale Research Letters, 2011, 6: 275, 9 pages.
Momot et al., "NMR Study of the Association of Propofol with Nonionic Surfactants", Langmuir, 2003, 19(6), pp. 2088-2095, Abstract.
Morey et al., "Preparation and Anesthetic Properties of Propofol Microemulsions in Rat", Anesthesiology, 2006, 104:6): 1184-1190.
Rodrigues et al., "A Comparative Study of Non-Lipid Nanoemulsion of Propofol with Solutol and Propofol Emulsion with Lecithin", Rev Bras Anestesiol, 2012; 62: 3: 325-334.
Ryoo et al., "Development of Propofol-loaded Microemulsion Systems for Parenteral Delivery", Arch Pharm Res, vol. 28, No. 12, pp. 1400-1404, (2005).

(Continued)

*Primary Examiner* — Shirley V Gembeh
(74) *Attorney, Agent, or Firm* — Vorys, Sater, Seymour and Pease LLP

(57) ABSTRACT

Provided is a novel dilutable delivery systems and propofol microemulsions suitable for intravenous delivery of propofol.

22 Claims, 10 Drawing Sheets

(56) References Cited

OTHER PUBLICATIONS

Spernath et al., "Microemulsions as carriers for drugs and nutraceuticals", Advances in Colloid and Interface Science, 128-130 (2006) 47-64.
Spernath et al., "Fully dilutable microemulsions embedded with phospholipids and stabilized by short-chain organic acids and polyols", Journal of Colloid and Interface Science, 299 (2006) 900-909.
Spernath et al., "Phosphatidylcholine embedded microemulsions: Physical properties and improved Caco-2 cell permeability", Journal of Controlled Release, 119 (2007) 279-290.
Spernath et al., "Phase Transition Induced by Water Dilution in Phospholipid U-Type Food-Grade Microemulsions Studied by DSC", Journal of Thermal Analysis and Calorimetry, vol. 83, (2006), 2, 297-308.

\* cited by examiner

DELIVERY SYSTEMS FOR PROPOFOL

TECHNOLOGICAL FIELD

The present invention concerns novel dilutable delivery systems suitable for intravenous delivery of propofol.

BACKGROUND OF THE INVENTION

Propofol (2,6-diisopropyl phenol, $C_{12}H_{18}O$) is a widely used drug for both intravenous anesthesia induction, as well as an agent for anesthesia maintenance by infusion administration. Propofol popularity has been gained due to its various advantages. Among the positive properties it offers is its rapid onset and short duration of action due to its low tendency to accumulate in the body (high clearance rate and relatively fast elimination due to its short half-life), combined with smooth and excellent emergence from anesthesia, with low incidence of postoperative nausea and vomiting. The fact that recovering from propofol anesthesia has minimal side effects had expanded its use from solely an anesthetic drug to a sedative-hypnotic agent used in the intensive care units, in outpatient procedures, and in adults on life-support systems.

Propofol is a lipophilic oil with virtually zero water solubility (150 µg/liter) and is therefore administered intravenously (IV) in an emulsion formulation. Development of propofol injected formulation has been a great challenge. The first clinical trials were conducted in Europe in 1977, using 1 and 2 wt % propofol preparations formulated with Cremophor EL and ethanol. This formulation had shown high anaphylaxis incidences causing the withdrawal of propofol from further development. Thereafter, many attempts to develop a formulation with minimal side effects and appropriate anesthetic profile, while maintaining the formulation's physical and chemical stability, were conducted. Finally, an oil-in-water (lipid-based) propofol emulsion was developed and evaluated for human use in clinical trials in Europe in 1983 and in the United States in 1984. This formulation was launched in the United Kingdom and New Zealand in 1986 and in the U.S. in 1989. In 1999 a generic lipid-based emulsion was also introduced to the U.S. market. In spite of FDA and European approvals of those emulsions, several major drawbacks were reported: physical emulsion instability, pain upon injection, hyperlipidemia (due to the relatively high lipid content) and increase possibility of microorganism contamination leading to blood sepsis complications and even death. In addition, propofol's sensitivity to oxidation and the emulsion's composition which is a substrate for proliferation of bacteria often dictates complicated production procedures and impose limitations on storage conditions and restrictions of usage after opening the emulsion vial. Further, the instability of the emulsion might cause, within time, to the formation of large droplets (over 500 nm) putting patients at risk, since the fused drops are too large to pass through the blood capillaries without causing emboli; the large fat globules formation is also extremely dangerous as it may remain relatively longer in the patient's organs, such as the lungs, spleen and liver, causing organ toxicity.

Contrary to most compounds administered intravenously, which are typically electrically charged molecules, propofol is not charged and therefore cannot be administered as an aqueous salt. Propofol's high lipophilicity and limited miscibility (150 µg/liter) has forced its formulation to be a lipid-based emulsion, containing soybean oil, egg yolk lecithin and glycerol. Although solving propofol's solubility problems, a substantial number of undesirable properties had been attributed to this large droplets emulsion system. The formulation had presented severe allergic reactions, physical instability and substantial pain during IV injection. In intensive care units, where propofol is used for long-term administration, the potential to develop hyperlipidemia is significant. This complication has been named "propofol infusion syndrome" and can often lead to lethal metabolic disorders. Moreover, the lipid formulation had shown a high risk of bacteremia due to its association with microbiology contamination during manufacture or throughout its preparation prior to its use. The failure to overcome the possibility of microbial growth, has led to the risk of patients developing high fever, infections, sepsis and even death. The high cost in propofol emulsion manufacturing, compared with alternative induction anesthesia agents, as well as the requirements to use propofol within 6 hours from opening had caused many propofol formulation manufacturers to seize production.

Because of its properties, propofol formulation presents a significant challenge to physical and colloid chemistry scientists. Some of the undesirable features of propofol are formulation-dependent. Consequently, there is a significant interest in the development of new formulations that will have minimal side effects and undesirable properties, however, will retain propofol's beneficial kinetic profile and its desirable anesthetic effect.

Microemulsions (MEs) can be considered as vehicles for drug delivery due to their spontaneous formation, high solubilization capacity and physical stability [1]. Attempts to formulate propofol in classical oil-in-water microemulsions have yet to be accepted by the pharmaceuticals industry or the FDA. To date, no acceptable formulations of fully dilutable propofol microemulsions that exhibit all the prerequisites for IV propofol preparations, e.g. dilutable by an aqueous phase, proper osmolarity, droplet size distribution, stability, microbiology clearance, pain-less, etc. were developed, which are essential for proper dispersion in blood without causing side effects or decomposing physically or chemically.

Nano-sized self-assembled liquids (NSSLs) are an advanced category of delivery vehicles. The NSSLs are self-assembled microemulsions systems of nanodroplets, comprising surfactants and oil. Such systems may comprise, at times, additional components such as co-surfactants, solvents, co-solvents and other additives. These self-assembled microemulsions may be in the form of concentrates that can be fully and progressively diluted with aqueous phase to form microemulsions. Upon formation, these systems self-assemble into reverse micelles; upon dilution with water or aqueous solutions, water-swollen micelles or water-in-oil nanodroplets are formed, being able to invert into bicontinuous mesophases in the presence of an aqueous phase, e.g. water. Upon further dilution, they undergo inversion (umbrella type inversion) into oil-in-water droplets. Such systems have been previously studied and their ability to solubilize non-soluble drugs and nutraceuticals has been demonstrated [2-7]. However, propofol's has unique chemical structure, being very lipophilic, and thus weakly interacts with the surfactant's head-groups and requires use of additional hydrophilic compounds to dehydrate the head-groups of the surfactants for obtaining elasticity, curvature and zero interfacial tension of the system. As a consequence to its unique properties, not every dilutable system provides for a stable propofol microemulsion that is suitable for parenteral administration.

In the present invention, nanometric structures, i.e. the improved self-assembled systems, are specially designed to load propofol in an oil concentrate, which can then be easily diluted "on demand" and as per application with any type of aqueous solution (buffer, water for injection, saline, isotonic mixtures and others). Unique tailoring of suitable self-assembled formulations for propofol according to the invention enable the drug-loaded concentrated formulation to be further diluted with fluid, such as the bloodstream, thereby forming clear (transparent), stable mixtures without phase separation and/or drug precipitation. These systems are isotropic, thermodynamically stable, presenting high solubilization capacity, and have an increased ability to improve the bioavailability of propofol. Other advantages of this unique formulation will become apparent from the disclosure below.

REFERENCES

[1] WO 2008/058366
[2] A. Spernath, A. Aserin, *Advances in Colloid and Interface Science* 2006, 128
[3] A. Spernath, A. Aserin, N. Garti, *Journal of Colloid and Interface Science* 2006, 299, 900-909
[4] A. Spernath, A. Aserin, N. Garti, *Journal of Thermal Analysis and Calorimetry* 2006, 83
[5] N. Garti, A. Spernath, A. Aserin, R. Lutz, *Soft Matter* 2005, 1
[6] A. Spernath, A. Aserin, L. Ziserman, D. Danino, N. Garti, *Journal of Controlled Release* 2007, 119
[7] WO 03/105607
[8] S. Davis, *Advance Clinical Nutrition* 1983, pp. 213-39

SUMMARY OF THE INVENTION

The present invention concerns an improved propofol-microemulsion suitable for intravenous delivery of propofol. The propofol may be loaded into a substantially water-free concentrate, that is dilutable by water or any other physiological liquid immediately prior to use, to result in a propofol-microemulsion suitable for parenteral administration. Alternatively, propofol-microemulsion of the invention may be provided in their diluted form, ready for immediate use. The unique combination of components in the propofol-concentrate, as well as the diluted propofol-microemulsion of the invention, greatly increases the chemical, biological and physical stability of the formulation over time, reduces the risk of contamination, broadens the scope of its application to a variety of concentrations (various doses) and diluted forms, while permitting the medical professionals to decide how, when and which formulation to prepare prior to use according to the specific need.

As one would appreciate, the propofol-concentrates and further products of the present invention provide for the first time a solution to a long felt need of providing a stable, high purity, water-free, yet water-dilutable propofol-containing products.

In the present invention, the tailored nanometric system allows for obtaining uniform size and shape of droplets, improved rheological properties, stability of the propofol (i.e. against oxidation), controllable droplets-to-air surface tension (spreadability), etc. In addition, the dilutable and diluted systems maintain the propofol in a bound state, namely eliminating free propofol; propofol is released from the system (either the concentrate or the diluted system) only upon further dilution, i.e. once introduced into the bloodstream. This, in turn, significantly reduces pain upon administration.

Thus, the invention provides microemulsions comprising propofol, as well as propofol-concentrates suitable for dilution, which form self-assembled systems (microemulsions). These self-assembled structures are poor in oil phase (propofol being the main oil phase), constituted by oil-solvated clusters or short domains of surfactants, however differ from the classical reverse micelles. When mixed with small amounts of aqueous media, a bicontinuous structure of solvated (oil-rich) and hydrated (water-rich) domains are formed; upon further dilution with aqueous phase, the bicontinuous structure progressively and continuously transforms into oil-in-water (O/W) nanodroplets entrapping the propofol molecules within their oily core (or within the surfactants tails). The transformation to O/W microemulsions is spontaneous, i.e. without the need to employ shear stresses or excessive heating conditions. The concentrates and microemulsions of the invention provide thermodynamically stable nano-structures (having nano-sized droplets), which may be safely stored for prolonged periods of time, without aggregation, coalescence or phase separation, compared to the instability and short shelf-life of the commercial propofol emulsions presently used. The propofol-microemulsion of the invention are also characterized by a substantially uniform and stable droplets size, typically having a narrow size distribution. The stability of the droplet size is of importance as changes in the droplet size may impair the release of the drug (on storage) and its anesthetic profile. Further, the propofol concentrate of the invention is devoid of water, and as such do not support (or minimize) microbial growth. Further, unlike commercial propofol emulsions or classical microemulsions, formulations of this invention show—due to careful tailoring of surfactants/co-solvents/co-surfactants composition—high chemical, biological and physical stability and small droplet size, is obtained. Further, formulations of the invention may be sterilized in various ways, such as heat sterilization, filtration through a 0.22 um filter, UV and other methods know to the art, without damaging the microemulsions' beneficial structure. Due to their inherent instability and need for multiple-step homogenization the exposure to contamination is greater, and sterilization via filtration is inefficient, due to the large droplet size, when carried out for commercial propofol emulsions.

In one of its aspects, the invention provides a propofol-microemulsion comprising an oil phase in the form of oil droplets dispersed in an aqueous diluent continuous phase, wherein the oil phase comprises propofol, at least one surfactant, at least one solvent, at least one co-surfactant, and at least one co-solvent, the oil droplets having a size of at most 20 nm in the continuous phase, the propofol and the surfactant having diffusion coefficients with the same order of magnitude when in the microemulsion composition (as measured by SD-NMR), and the microemulsion being suitable for parenteral administration.

In the context of the present disclosure the term diffusion coefficient denotes the relative rate of diffusion of one material into another material. A characteristic of the microemulsions of this disclosure, is the similarity between the diffusion coefficients of the propofol and the surfactant when present in the microemulsion, and as measured by SD-NMR (as will be described below). When the diffusion coefficients of propofol and the surfactant are of the same order of magnitude, the propofol will substantively have no driving force to diffuse out of the oil droplet, thereby maintaining the propofol within the oil droplet (i.e. within the core and/or the interface with the diluent). Since free propofol in known to be the cause of pain upon injection, the fact that propofol is located within the oil droplets is expected to significantly reduce pain and irritation during and following administration. In addition, the location of the propofol within the core or/and interface of the oil droplets (having similar SD-NMR values of surfactant-propofol) results in its ability to be released from the nano-droplet in such a manner that will lead to the quick dispersity of the propofol in the bloodstream, resulting in the desirable fast anesthesia induction and maintenance (as can be seen in the animal study).

In some embodiments, the diffusion coefficients of propofol and the surfactant (when in the microemulsion) are at least of one order of magnitude smaller than the other components of the microemulsion.

In other embodiments, the diffusion coefficients of propofol and the surfactant (when in the microemulsion) are of an order of magnitude of $1\times10^{-11}$ m$^2$/sec, when in the microemulsion specific combination, as measured by SD-NMR. In some other embodiments, the diffusion coefficients of propofol and the surfactant (when in the microemulsion) are of an order of magnitude of $1\times10^{-10}$ m$^2$/sec, $1\times10^{-9}$ m$^2$/sec or even $1\times10^{-8}$ m$^2$/sec when in the microemulsion specific combination, as measured by SD-NMR.

The surfactant may be selected from any type of suitable surfactant that fulfils the diffusion coefficient requirement within the microemulsion composition. These may include, ionic, cationic or zwitterionic or non-ionic surfactants having a hydrophilic nature, i.e. a surfactant having an affinity for water. Exemplary surfactants are polyoxyethylene sorbitan monolaurate, polyoxyethylene sorbitan monopalmitate, polyoxyethylene sorbitan monooleate, and polyoxyethylene esters of saturated and unsaturated castor oil, ethoxylated monoglycerol esters, ethoxylated fatty acids and ethoxylated fatty acids of short and medium and long chain fatty acids and others. Hydrophilic phospholipids such as lysophosphatudyl choline and other similar phospholipids.

The list of hydrophilic surfactants include at least one of the hydrophilic surfactant from polyoxyethylenes, ethoxylated (20EO) sorbitan mono laurate (T20), ethoxylated (20EO) sorbitan monostearate/palmitate (T60), ethoxylated (20EO) sorbitan mono oleate/linoleate (T80), ethoxylated (20EO) sorbitan trioleate (T85), castor oil ethoxylated (20EO to 40EO); hydrogenated castor oil ethoxylated (20 to 40EO), ethoxylated (5-40 EO) monoglyceride stearate/palmitate, polyoxyl 35 and 40 EOs castor oil. According to other embodiments, the hydrophilic surfactant may be selected from polyoxyl 35 castor oil, polysorbate 40 (Tween 40), polysorbate 60 (Tween 60), polysorbate 80 (Tween 80), Mirj S40, Oleoyl macrogolglycerides, Polyglyceryl-3 dioleate, ethoxylated hydroxyl stearic acid (Solutol HS15), sugar esters such as sucrose mono oleate, sucrose mono laurate, sucrose mono stearate. Polyglycerol esters such as deca glycerol mono oleate or monolaurate, hexa glycerol monolaurate or mono oleate.

In some embodiments the hydrophilic surfactant may be mixed with certain amounts of lipophilic surfactants such as sorbitan mono stearate, sorbitan monooleate, sorbitan tri stearate or tri oleate, polyglycerol esters sucha mono and tri glycerol esters of stearic acid or palmitic acid or lauric or oleic and their mixtures. Sucrose esters such as sucrose di and tri fatty acid esters and any type of phospholipids.

In some embodiments, the surfactant may be polyethylene glycol 15-hydroxystearate (Solutol HS 15). In other embodiments, the surfactant may be a polyoxyethylenes such as a polysorbate (polyoxyethylene sorbitan monolaurate, such as Tween 40, Tween 60, Tween 80, etc.)

In one of its aspects, the invention provides a propofol-microemulsion comprising an oil phase in the form of oil droplets dispersed in an aqueous diluent continuous phase, wherein the oil phase comprises propofol, polyethylene glycol 15-hydroxystearate (Solutol HS 15), at least one solvent, at least one co-surfactant, and at least one co-solvent, the oil droplets having a size of at most 20 nm in the continuous phase, and the microemulsion being suitable for parenteral administration.

In another of its aspects, the invention provides a propofol-microemulsion comprising an oil phase in the form of oil droplets dispersed in an aqueous diluent continuous phase, wherein the oil phase comprises propofol, a polysorbate, at least one solvent, at least one co-surfactant, and at least one co-solvent, the oil droplets having a size of at most 20 nm in the continuous phase, and the microemulsion being suitable for parenteral administration.

In some embodiments, the microemulsions are characterized by a mono-disperse size distribution of oil droplets.

In some embodiments, the droplet size and uniform distribution is obtained at a water dilution in the range of about 70 to 93 wt % water.

Propofol-microemulsions of the invention are defined as spontaneously formed oil-in-water (O/W) microemulsions, in which the diluent forms the continuous phase, while the oil phase is in the form of discrete droplets of nanometric size. In the context of the present invention, the term propofol-microemulsion refers to thermodynamically stable self-assembled nano-droplets or other structures of immiscible oil which solubilizes propofol and water or water-like liquid dispersions, i.e. those having an average droplet diameter of at most 20 nanometers (nm). The propofol-microemulsions of this invention have substantially zero interfacial tension between the oil droplets and the aqueous diluent, thereby enabling self-assembly and continuous dilutability.

It should be emphasized that propofol-microemulsions of the invention are those spontaneously formed, without the need to apply high shearing, cavitation or high-pressure homogenization processes, but rather upon simple mixing of the microemulsions' components at low mixing rates. Thus, in some embodiments, propofol-microemulsions of the invention are prepared by diluting propofol-concentrates (the formulations and properties of which will be discussed herein) with a suitable diluent, e.g. water, without application of shearing, cavitation or homogenization conditions.

In some embodiments, the oil droplets size of the microemulsion is between about 10 and 20 nm (nanometers). The droplet size refers to the arithmetic mean of measured droplets' diameters, wherein the diameters range±15% from the mean value.

In some other embodiments, the droplet size may be between about 15 and 17 nm.

Further, propofol-microemulsions of the invention are characterized by a mono-disperse size distribution of the oil droplets. Namely, the size distribution of the oil droplets in propofol-microemulsions of the invention is narrow, without significant divergence from the mean size value. In some embodiments, the polydispersity index (PDI) of the distribution of oil droplets is between about 0.03 and 0.08.

As noted above, in microemulsions of the invention, propofol is stably contained (i.e. solubilized) within the oil droplets due to the use of a surfactant that has a diffusion coefficient similar to that of propofol within the microemulsion composition. Example of such surfactants are Solutol and polysorbate (e.g. Tween 60 or Tween 80) and the solvent, and is controllably released into the bloodstream after administration. Without wishing to be bound by theory, the propofol-surfactant-solvent system forms strong molecular interactions, thus permitting solubilization of propofol within the oil droplets of the microemulsion. The combination of the surfactant and propofol in the presence of the solvent provides for interactions between the surfactant and the propofol (i.e. physical binding of the propofol to the surfactant molecules), thereby inhibiting and/or preventing propofol from migrating from the core to the oil-water interface or its release into the aqueous phase upon storage. Upon high dilutions, i.e. when introduced into the bloodstream, a micellar system is formed, thereby enabling (because of its dynamic structure) the release of propofol from the oil droplet the bloodstream and thereafter to obtain the desired anesthetic effect via diffusion across the blood brain barrier (BBB). In other words, prior to introduction to the bloodstream substantially no propofol is present in the continuous diluent phase, thereby preventing undesired pain and discomfort in the area of and during intravenous administration.

Pain during administration is also minimized due to the small size of the droplets and their size uniformity. Such uniformity also allows for controlled and stable release of the propofol in the bloodstream following administration, as well as permits controlled clearance of the components from the bloodstream.

Propofol-microemulsions of the invention are suitable for parenteral administration to a patient in need thereof. Parenteral routes of administration enable total systemic availability and fastest onset of action. The most commonly used parenteral routes are intravenous (i.v.), intramuscular (i.m.), and subcutaneous (s.c.). Intravenous injection offers rapid onset of anesthesia, which is the typical route of administration of propofol, although consecutive drip administration of propofol (constant infusion) is also used to maintain constant drug levels in patients in need thereof (e.g. continued anesthesia or mild sedating).

The diluent in the microemulsions is typically a pharmaceutically acceptable aqueous medium, constituting the continuous phase. In some embodiments, the diluent is selected from water, water for injection, saline, dextrose solution, or a buffer having a pH between 3 and 9 or any other isotonic solution suitable for parenteral administration.

In the context of the present disclosure, the term solvent refers to any organic solvent suitable for assisting the solubilization of propofol, and approved for administration to a mammal, including mineral oil, paraffinic oils, vegetable oils, glycerides, fatty acids, esters of fatty acids, liquid hydrocarbons and alcohols thereof, and others.

According to some embodiments, the solvent may be selected from medium-chain triglycerides (MCT), olive oil, soybean oil, canola oil, cotton oil, palmolein, sunflower oil, corn oil, isopropyl myristate, oleyl lactate, coco caprylo-caprate, hexyl laurate, oleyl amine, oleic acid, oleyl alcohol, linoleic acid, linoleyl alcohol, ethyl oleate, hexane, heptanes, nonane, decane, dodecane, D-limonene, neem oil, lavender oil, peppermint oil, anise oil, mentol, capsaicin and similar essential oils and mixtures thereof.

According to other embodiments, the solvent is at least one medium-chain triglyceride (MCT).

In some embodiments, the microemulsion comprises propofol, Solutol HS 15, MCT, at least one co-surfactant, at least one co-solvent, and an aqueous diluent.

Propofol-microemulsions of the invention also comprise at least one co-surfactant. The term co-surfactant should be understood to encompass any agent, different from the surfactant, which is capable (together with the surfactant) of lowering the interfacial tension between the oil phase and the aqueous phase to almost zero (or zero) allowing for the formation of a homogeneous oily mixture. According to some embodiments, the co-surfactant is selected from polyols, diglycerides, polyoxyethylenes, lecithins, phospholipids such as DOPC, Epicoron 200, POPC, and others.

In some embodiments, the co-surfactant may be at least one "polyol", i.e. an alcohol containing at least 2 hydroxyl groups. In such embodiments, the at least one polyol may be selected from ethylene glycol, glycerol, polyethylene glycol, polypropylene glycol, sorbitol, manitol, lactitol and xylitol.

In other embodiments, the polyol is selected from glycerol, polypropylene glycol, polyethylene glycol and mixtures thereof.

Suitable diglycerides which may be used in accordance with the present invention include glycerol diesters of short or medium or long, or saturated or mono or poly unsaturated chain fatty acid, di-unsaturated $C_{6-20}$ fatty acids, polyoxyethylenes, ethoxylated (20EO) sorbitan mono laurate (T20), ethoxylated (20EO) sorbitan monostearate/palmitate (T60), ethoxylated (20EO) sorbitan mono oleate/linoleate (T80), ethoxylated (20EO) sorbitan trioleate (T85), castor oil ethoxylated (20EO to 40EO); hydrogenated castor oil ethoxylated (20 to 40EO), ethoxylated (5-40EO) monoglyceride stearate/palmitate.

Exemplary polyoxyethylene surfactants are polyoxyethylene sorbitan monolaurate, polyoxyethylene sorbitan monopalmitate, polyoxyethylene sorbitan monooleate, and polyoxyethylene esters of saturated and unsaturated castor oil, ethoxylated monoglycerol esters, ethoxylated fatty acids and ethoxylated fatty acids of short and medium and long chain fatty acids and others.

Phospholipids such as soy lecithin, rapeseed lecithin, corn or sunflower lecithins, egg lecithin, dioleyl phosphatidylcholine, oleyl palmytoyl phosphatidylcholine and the corresponding serines, ethanol amines, glycerol, and others, may also be used.

Co-solvents used in the microemulsions of the invention are agents which assist the solubilization of propofol in the oil phase. According to some embodiments, the co-solvent is selected from ethanol, propanol, propylene glycol and glycerol.

In some embodiments, the co-surfactant and the co-solvent may be the same, i.e. constituted by the same component having both functionalities. In other embodiments, the co-solvent and the co-surfactant are different chemical components.

The unique combination of propofol, surfactant and the rest of the microemulsions' components provides for excellent physical, chemical and thermal stability of the propofol-microemulsions, as well as excellent control of the microemulsions' oil droplet size. In addition, the propofol and the surfactant are bound to one another by relatively strong hydrogen bonds or other physical interactions, thus minimizing the free (un-bound) propofol in the microemulsion, thereby reducing the undesired side-effects (such as pain) during administration. The hydrogen bonds also enable slow release and/or controlled release of the propofol from the microemulsion to the bloodstream after administration.

In some embodiments, the propofol-microemulsion comprises at least 2 co-surfactants. In such embodiments, the co-surfactants may be at least 2 polyols. A non-limiting example of such microemulsion comprises both propylene glycol (PG) and polyethylene glycol (PEG). Co-surfactants such as PG are used in order to obtain zero interfacial tension along the entire dilution line, thereby providing for continuous and progressive dilution of the propofol-microemulsion by the diluent, as well as assisting in maintaining the integrity of the nano-structures. Co-surfactants such as PEG or glycerol provide better binding of the propofol in the oil phase within the swollen micelles formed during dilution, thereby further maintaining the propofol within the micelles prior to introduction into the bloodstream.

Thus, in some embodiments, the propofol-microemulsion comprises propofol, Solutol HS 15, MCT, polyethylene glycol, propylene glycol, a co-solvent, and an aqueous diluent.

In other embodiments, the propofol-microemulsion comprises propofol, a polysorbate, MCT, polyethylene glycol, propylene glycol, a co-solvent, and an aqueous diluent.

In some other embodiments, the propofol-microemulsion is devoid of polyethylene glycol.

In some embodiments, the propofol-microemulsion comprises propofol in a concentration of between about 0.1 and 2 wt %. In some other embodiments, this concentration is between about, 0.1 and 1.75 wt %, 0.1 and 1.5 wt %, 0.1 and 1.25 wt %, 0.1 and 1 wt %, 0.1 and 0.75 wt %, or 0.1 and 0.5 wt % of the microemulsion. In further embodiments, the concentration is between about 0.5 and 2 wt %, 0.75 and 2 wt %, 1 and 2 wt %, or 1.25 and 2 wt % of the microemulsion.

According to some embodiments, the propofol-microemulsion comprises about 1 wt % propofol.

According to other embodiments, the propofol-microemulsion of the invention comprises between about 75 and 98 wt % of diluent. Namely, the diluent may constitute about 75, 80, 85, 90, 95, 97, or even 98 wt % of the microemulsion's composition.

As noted above, the droplet size and stability of the propofol in the microemulsion are predominantly obtained by using the surfactant, and at least one solvent. Propofol is fully solubilized in the solvent and interacts with the surfactant via reversible hydrogen bonds. These interactions maintain the propofol within the oil droplet (i.e. as micelles), preventing its release into the continuous phase and minimizing pain and irritation at the administration site. Once within the blood system, propofol is quickly released from the micelles, allowing rapid anesthesia effect. As a man of the art may appreciate, the ratio between these components may be tailored according to the nature of the solvent and the desired propofol loading, and may also be selected for endowing certain characteristics to the microemulsion (such as, desired particle size and electrical charge).

Thus, in some embodiments, the weight ratio (i.e. w/w ratio) between propofol and the surfactant is between about 1:5 and 1:12. In such embodiments, the ratio between propofol and the surfactant may be between about 1:5.5 and 1:12, 1:6 and 1:12, 1:6.5 and 1:12, 1:7 to 1:12 or even 1:7.5 and 1:12. In other such embodiments, the ratio between propofol and the surfactant may be between about 1:5 and 1:11.5, 1:5 and 1:11, 1:5 and 1:10.5, 1:5 and 1:10, 1:5 and 1:9.5 or even 1:5 and 1:9. In some other embodiments, the ratio between propofol and surfactant may be 1:5, 1:5.5, 1:6, 1:6.5, 1:7, 1:1.75, 1:8, 1:8.5, 1:9, 1:9.5, 1:10, 1:10.5, 1:11, 1:11.5 or 1:12.

According to some embodiments, the weight ratio between said at least one solvent and the surfactant is between about 1:8 and 1:12. In such embodiments, the ratio between the at least one solvent and the surfactant may be between about 1:8.5 and 1:12, 1:9 and 1:12, or even 1:9.5 and 1:12. In other such embodiments, the ratio between the at least one solvent and the surfactant may be between about 1:8 and 1:11.5, 1:8 and 1:11, or even 1:8 and 1:10.5. In some other embodiments, the ratio between the at least one solvent and the surfactant may be 1:8, 1:8.5, 1:9, 1:9.5, 1:10, 1:10.5, 1:11, 1:11.5 or 1:12.

In some embodiments, the weight ratio between said at least one solvent and propofol is between about 1:2 and 1.25:1. In such embodiments, the ratio between the at least one solvent and propofol may be between about 1:1.8 and 1.25:1, 1:1.6 and 1.25:1, 1:1.4 and 1.25:1, 1:1.2 and 1.25:1, or even or 1:1 and 1.25:1.

In other such embodiments, the ratio between the at least one solvent and propofol may be between about 1:2 and 1.2:1, 1:2 and 1.15:1, 1:2 and 1.1:1, or even 1:2 and 1.05:1. In some other embodiments, the ratio between the at least one solvent and the propofol may be 1:2, 1:1.66, 1:1.43, 1:1.2, 1:1, 1.1:1, 1.2:1.1, or 1.25:1.

The propofol-microemulsions of this disclosure may further comprise additives, such as pH adjusting agents (e.g. NaOH).

In contrast to the milky white commercial emulsions comprising propofol, propofol-microemulsions of the present invention are, by some embodiments, transparent due to their mono-dispersed nanometer droplet size and high stability, and maintain their transparency for a prolonged period of time. The small droplet size of the propofol-microemulsions of the invention, which are less than one fourth of the average wavelength of visible light (0.560 micrometer), appear to the naked eye as a clear and homogenous liquid, lacking any observable clouding or areas of phase separation. In some embodiments, the propofol-microemulsion has a turbidity value of between about 20 and 70 NTU (nephelometric turbidity units). In other embodiments, the turbidity value is between 20-40 NTU. In contrast to lipid-based commercial emulsions, in which the unaided eye cannot detect the formation of large oil globules due to the opaqueness of the emulsion, the transparency of the propofol-microemulsion allows easy detection of changes in its stability (as phase separation and/or coalescence of oil droplets will cause detectable clouding). Further, growth of bacteria will also cause changes in transparency and turbidity, thereby enabling straight-forward detection of contamination.

In some embodiments, the propofol-microemulsions of the invention have an osmolality value of between about 250 and 450 mOsm/Kg (milli-osmoles per kilogram), being similar to the physiological osmolality of the bloodstream, thereby limiting hemolytic effect, pain and a staining sensation upon administration. The osmolality is the concentration of particles dissolved in solution expressed, and is indicative of the osmotic pressure of a solution. In some embodiments, the osmolarity is between about 250 and 350 mOsm/Kg.

While typical propofol emulsions of the art are characterized by an absolute droplet-air tension (i.e. microdroplets surface tension against air) of approximately 36-45 mN/m (millinewtons per meter), propofol-microemulsions of the invention, by some embodiments, have a surface tension of between about 27 and 35 mN/m. These low interfacial and surface tensions allow better distribution of the propofol-loaded microemulsion within the bloodstream and potentially better transport across the blood brain barrier required for fast onset of propofol.

In a further difference from emulsions of the art, in some embodiments propofol-microemulsions of the invention demonstrate the behavior of a Newtonian liquid. Namely, the pressure or shear forces developed in the microemulsion during flow are linearly proportional to the rate of flow. This enables easy prediction of the flow properties, thereby allowing better control of the microemulsion flow.

As already noted above, propofol-microemulsions of the invention may be formed by diluting propofol-concentrates with a suitable diluent. Thus, in another aspect, the invention provides a dilutable propofol-concentrate comprising 2,6-diisopropyl phenol (propofol), a surfactant, at least one solvent, at least one co-surfactant, and at least one co-solvent, the concentrate being substantially free of water.

In another aspect, the invention provides a dilutable propofol-concentrate comprising 2,6-diisopropyl phenol (propofol), polyethylene glycol 15-hydroxystearate (Solutol HS 15), at least one solvent, at least one co-surfactant, and at least one co-solvent, the concentrate being substantially free of water.

In another aspect, the invention provides a dilutable propofol-concentrate comprising 2,6-diisopropyl phenol (propofol), a polysorbate, at least one solvent, at least one co-surfactant, and at least one co-solvent, the concentrate being substantially free of water.

The term propofol-concentrate denotes a substantially (at times entirely) water-free, oil-based structured lipid/surfactant system, in which surfactant tails are solubilized by the propofol and the solvent, facilitating full dilution by a diluent aqueous phase (are dilutable) at will to form propofol-microemulsions of the invention. In other words, the propofol-concentrates of the invention are designed for fast and complete dilution in a suitable diluent, typically water for injection or saline, forming the propofol-microemulsions (as a self-assembled nanostructured system). Due to the combination of surfactant, solvent, co-surfactant and co-solvent, the propofol-concentrate system of the invention is capable of solubilizing high contents of propofol, e.g. up to 12 wt %. Upon dilution with a suitable diluent, the propofol-concentrate of the invention spontaneously forms microemulsions, which are at first solvated domains (or clusters) of surfactant mesophases, that upon dilution (ca. 20-30 wt %) form water-in oil nanodroplets; upon further dilution transform to bicontinuous mesophases and into oil-in-water (O/W) nanodroplets, in which the diluent forms the continuous phase, while the oil phase is in the form of discrete droplets of nanometric size (i.e. the microemulsions of the invention). As noted above, the propofol-microemulsions are formed from the concentrate spontaneously, namely without the need to apply any shear, cavitation or homogenization processes, due to the balance of surface energies obtained by the selection of components of the system.

In order to overcome the high contamination rate of presently available commercial propofol-based formulae, the propofol-concentrates of the invention are substantially free, i.e. devoid, of water. Once water is absent from the formulation, concentrates of the invention lack the environment sustaining microorganisms growth (e.g. fungi or bacteria), permitting longer storage without (or with minimal) risk of contamination. Without wishing to be bound by theory, one of the reasons due to which almost no bacterial contamination is observed for systems of the invention may be the absence of unbound water. Compared to propofol emulsions which contain a high concentration of free water and thus support microbial growth, the propofol-microemulsions of the invention (including those formed from the propofol-concentrate) do not contain a large amount of free (i.e. unbound) water, and thus limit microbial growth.

In some embodiments, the dilutable concentrates are entirely devoid of water (i.e. water-free).

The dilutable propofol-concentrate of the invention typically comprise between about 3-12 wt % propofol, i.e. 3, 4, 5, 6, 7, 8, 9, 10, 11 or 12 wt % propofol. In some embodiments, the propofol-concentrate comprises about 4-12 wt %, 5-12 wt %, 6-12 wt %, 7-12 wt %, 8-12 wt % or 9-12% propofol. In other embodiments, the propofol-concentrate comprises about 3-11 wt %, 3-10 wt %, 3-9 wt %, 3-8 wt %, or 3-7 wt % propofol.

According to additional embodiments, the propofol-concentrate comprises about 6-11 wt % propofol.

In some embodiments, the weight ratio between propofol and the surfactant in the propofol-concentrate is between about 1:5 and 1:12.

In other embodiments, the weight ratio between said at least one solvent and the surfactant in the propofol-concentrate is between about 1:8 and 1:12.

In some other embodiments, the weight ratio between said at least one solvent and propofol in the propofol-concentrate is between about 1:2 and 1.25:1.

In some embodiments, the solvent in the propofol-concentrate is selected from mineral oil, paraffinic oils, vegetable oils, glycerides, fatty acids, esters of fatty acids, liquid fatty alcohols and liquid fatty acids liquid hydrocarbons and alcohols thereof, and waxes. In such embodiments, the solvent is selected from medium-chain triglycerides (MCT), olive oil, soybean oil, canola oil, cotton oil, palmolein, sunflower oil, corn oil, isopropyl myristate, oleyl lactate, coco caprylocaprate, hexyl laurate, oleyl amine, oleic acid, oleyl alcohol, linoleic acid, linoleyl alcohol, ethyl oleate, hexane, heptanes, nonane, decane, dodecane, and mixtures thereof.

In other embodiments, the co-surfactant in the propofol-concentrate may be selected from polyols, diglycerides, polyoxyethylenes, and lecithins. In such embodiments, the co-surfactant may be at least one polyol selected from ethylene glycol, glycerol, polyethylene glycol, polypropylene glycol, sorbitol, manitol, lactitol and xylitol.

In some other embodiments, the co-solvent in the propofol-concentrate is selected from ethanol, propanol or glycerol.

In another aspect there is provided a dilutable propofol-concentrate comprising propofol, Solutol HS 15, MCT, polyethylene glycol, propylene glycol, and a co-solvent, the concentrate being substantially free of water.

In another aspect there is provided a dilutable propofol-concentrate comprising propofol, polysorbate, MCT, polyethylene glycol, propylene glycol, and a co-solvent, the concentrate being substantially free of water.

In some embodiments, the co-solvent is ethanol.

Where applicable, where parenteral administration is desired, the water-free propofol-concentrate of the invention form the basis of the propofol-microemulsions.

A further aspect of the invention provides a pharmaceutical composition suitable for parenteral administration, comprising the dilutable concentrate of the invention as herein described and a suitable pharmaceutically acceptable aqueous diluent.

A microemulsion formulation suitable for parenteral (e.g. intravenous) administration may further comprise aqueous and non-aqueous, isotonic sterile injectable solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, preservatives and buffers.

In some embodiments, the propofol-microemulsion formulation (and/or the dilutable propofol-concentrate) may comprise antioxidants, for examples, such selected compounds which blocks the chain reaction by reacting with the free radicals (such as tocopherol or its derivatives, i.e. tocopherol acetate), reducing agents or antioxidant that can lower the redox potential of the propofol and prolong the drugs stability (such as ascorbic acid or ascorbyl palmitate), antioxidants synergists which enhance the antioxidants activity, and others.

In other embodiments, the propofol-microemulsion formulations may comprise excipients enable further inhibition of bacterial and fungal growth, such as those selected from EDTA (disodium ethylenediametetraacetate), sodium metabisulfite, tromathamine, pentetate, benzyl alcohol, benzethonium chloride and sodium benzoate and other antimicrobial agents known to the art.

Another aspect of the invention provides the use of a dilutable propofol-concentrate for the preparation of a composition (microemulsion) for parenteral administration of propofol.

The invention further provides, in another aspect, a process for preparing a composition suitable for parenteral administration of propofol, comprising diluting a propofol-concentrate of the invention as herein described in a predetermined quantity of a suitable diluent, such as water, saline, dextrose solution, or a buffer having a pH between 3 and 9. In some embodiments, the predetermined quantity of diluent is between about 75-98 wt % of the propofol-microemulsion.

In another aspect, the invention provides a kit comprising means for holding a dilutable propofol-concentrate of the invention and at least one other means for comprising a diluents, and instructions of use.

The term "means for holding" refers to a compartment or a container or a discrete section of a vessel, separated from the other for holding or containing the various components of the kit. Within the context of the present invention, the term also refers to separate containers or vessels, housed within a single housing.

Each one of the containers may be of single or multiple-dose contents. The containers may be in any form known in the art, such as syringes, vial, ampoules, collapsible bags, bottles, etc, enabling immediate use or on-site preparation of the microemulsion by the addition of the diluent, for example, water for injections, immediately prior to use.

As propofol is known to relatively easily oxidize, the preparation of the propofol-concentrates, propofol-microemulsions or filling of the containers may be, in some embodiments, carried out under inert environment (e.g. argon, nitrogen or other inert gases).

In some embodiments, the kit comprises instructions for use and/or at least one measuring tool, for measuring the weight, volume or concentration of each component.

According to another aspect, the invention provides a method for parenteral administration of propofol to a subject in need thereof, the method comprising diluting a dilutable propofol-concentrate of the invention as herein described to a predetermined effective amount in a suitable diluent, thereby obtaining a composition suitable for parenteral administration (i.e. the propofol-microemulsion), and administering said composition intravenously to said subject.

As known, the "effective amount" for purposes herein may be determined by such considerations as known in the art. The effective amount is typically determined in appropriately designed clinical trials (dose range studies) and the person versed in the art will know how to properly conduct such trials in order to determine the effective amount. As generally known, the effective amount depends on a variety of factors including the distribution profile within the body, a variety of pharmacological parameters such as half-life in the body, on undesired side effects, if any, on factors such as age and gender, and others.

In some embodiments, the suitable diluent is water, water for injection, saline or dextrose solution, and said predetermined effective amount is between about 0.1 and 2 wt % of active compound in the composition.

The term "subject" refers to a mammal, human or non-human.

In another aspect, the invention provides a method of inducing an anesthetic effect to a subject in need thereof, comprising administering to the subject a propofol-microemulsion as described herein.

The term anesthetic effect refers to any form of sedation of a subject, suppressing the central nervous system and/or causing local blockage of nerve impulses between an organ and the central nervous system. The term means to include general anesthesia, regional anesthesia, local anesthesia, peripheral blockade, neuroaxial blockade (such as epidural or spinal anesthesia), and sedation. The anesthetic effect may be obtained by administering the microemulsion described herein in any dosage regimen suitable for obtaining the desired anesthetic effect. Depending on the effect desired, the propofol-microemulsion may be administered as bolus doses, local injection, continuous infusion, etc.

As noted above, the unique binding between propofol and the surfactants forming the oil phase of the microemulsion causes localization of the propofol within the oil droplet, and controlled release thereof only upon further dilution in the bloodstream post-administration. As propofol is known as an irritant, that often causes pain and/or stinging sensation in the administration site, such binding minimizes the presence of free propofol during administration, thereby significantly reducing its irritancy effect.

Thus, in another aspect, this disclosure provides a method for preventing irritancy or reducing pain during administration of propofol in a site of administration, the method comprising providing a propofol-microemulsion of this disclosure, and administering the propofol-microemulsion to a patient in need thereof at a site of administration, the propofol being maintained within the oil droplets of the microemulsion during administration. The term irritancy means to denote local inflammation of the tissue surrounding the administer site (i.e. direct irritation), as well as an allergic response due to interaction of the immune system to propofol (namely, non-direct irritation).

As demonstrated further below, propofol-microemulsions of this disclosure showed a significantly reduced response to pain in a paw-licking model as compared to commercial propofol emulsion formulations in which no propofol-surfactant interactions exit.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between. It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

As used herein, the term "about" is meant to encompass deviation of ±10% from the specifically mentioned value of a parameter, such as temperature, pressure, concentration, etc.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1B: B6A formulation), compared to a propofol lipid emulsion prepared by high-shear mixing (or cavitation) according to Example 1 of reference [1] (FIG. 1C).

DETAILED DESCRIPTION OF EMBODIMENTS

Figure 1A:
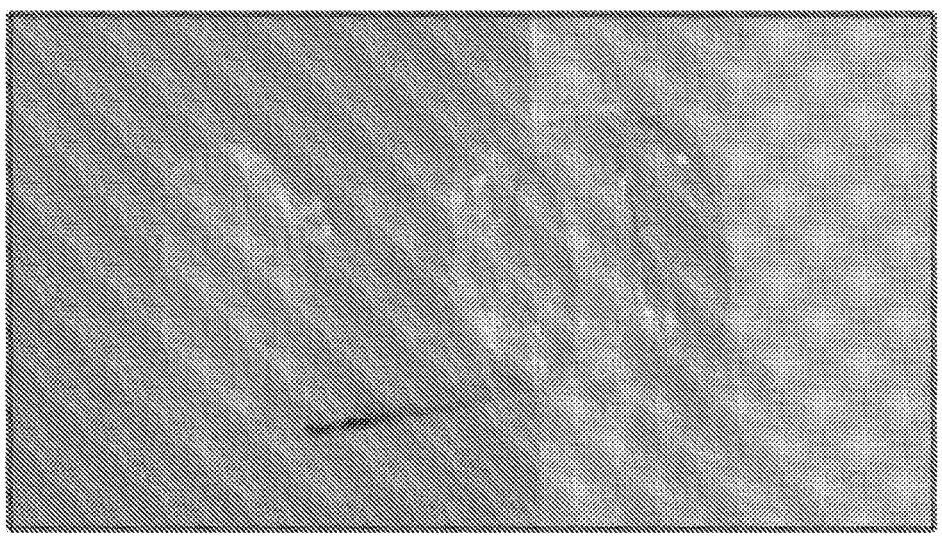
FIGS. 1A-1C shows a propofol microemulsion of the invention (FIG. 1A: B9A formulation.

Example I: Propofol-Microemulsions Compared to Commercial Emulsions 1 wt % propofol commercial liquid emulsion (CLE) Propofol-Lipuro® 1% was used as reference for comparison with the propofol-microemulsions of the invention.

Two dilutable propofol-concentrates were prepared, containing 6 wt % and 9 wt % of propofol (B6 and B9, accordingly), according to the following preparation protocol.

B6 Concentrate

Solutol HS-15 (also known as Kolliphor HS-15) was heated to about 40-60° C. Following heating, the Solutol was introduced into a vessel, together with propylene glycol (PG), MCT, polyethylene glycol 400 (PEG 400) and ethanol, and mixed for 10 minutes at 50-400 rpm. Egg Lecithin E80 (egg phospholipids with 80% phosphatidylcholin) was added, and mixed for 60 minutes, at 40-50° C. and mixed at 50-400 rpm. The mixture was then left to cool down to room temperature. Once the mixture has cooled, propofol was added and mixed form 5-30 minutes at 50-400 rpm, to thereby obtain a concentrate containing 6 wt % propofol.

B9 Concentrate

Solutol HS-15 (also known as Kolliphor HS-15) was heated to about 40-60° C. Following heating, the Solutol was introduced into a vessel, together with propylene glycol, MCT, PEG 400 and ethanol, and mixed for 10 minutes at 50-400 rpm. Propofol was then added and mixed form 5-30 minutes at 50-400 rpm, to thereby obtain a concentrate containing 9 wt % propofol.

B10 and B11 compositions, containing 10 and 11 wt % propofol, respectively, were prepared in a similar manner Compositions of the concentrates are detailed in Table 1.

In order to obtain the propofol-microemulsions, the concentrates were diluted with an appropriate amount of water for injection for 20-60 minutes at 200-400 rpm, to obtain microemulsions having a propofol concentration of 1 wt %. It is of note that preparation of larger batches of concentrate and/or microemulsion may be carried out under inert atmosphere (such as a flow of nitrogen) in order to prevent oxidation of propofol. The compositions of the microemulsions are detailed in Table 2.

TABLE 1

Dilutable propofol-concentrate compositions, 6-11 wt % propofol

| | Solutol | PG | MCT | PEG 400 | Ethanol | Lecithin | Propofol |
|---|---|---|---|---|---|---|---|
| B6 | 70.246 | 1.88 | 7.52 | 7.52 | 4.954 | 1.88 | 6 |
| B9 | 68.203 | 3.688 | 6.08 | 6.949 | 6.08 | 0 | 9 |
| B10 | 65.537 | 3.646 | 6.014 | 6.87 | 7.933 | 0 | 10 |
| B11 | 60.113 | 6.955 | 5.945 | 6.797 | 9.190 | 0 | 11 |

*All quantities in wt %.

TABLE 2

Propofol-microemulsions, 1 wt % propofol

| | Solutol | PG | MCT | PEG 400 | Ethanol | Lecithin | Propofol | Water |
|---|---|---|---|---|---|---|---|---|
| B6A | 11.707 | 0.313 | 1.253 | 1.253 | 0.825 | 0.313 | 1 | 83.333 |
| B9A | 7.578 | 0.409 | 0.675 | 0.772 | 0.675 | 0 | 1 | 88.88 |
| B10A | 6.554 | 0.365 | 0.601 | 0.687 | 0.793 | 0 | 1 | 90.00 |
| B11A | 5.465 | 0.632 | 0.540 | 0.618 | 0.835 | 0 | 1 | 90.91 |

*All quantities in wt %.

The physical properties of propofol-microemulsions prepared from B6, B9, B10 and B11 concentrates, in comparison to CLE, are provided in Tables 3-1 and 3-2.

TABLE 3-1

Properties of B6 and B9 based microemulsions compared to commercial lipid emulsion (CLE)

| Parameter | Microemulsion prepared from propofol concentrate | | |
|---|---|---|---|
| | B6A | B9A | CLE |
| Transparency | Yes | Yes | No |
| Color | Clear yellowish | Clear yellowish | White opaque |
| Microscopy[a] | Uniform | Uniform | Uniform |
| Turbidity (NTU)[b] | 26.2 | 38.18 | NA |
| pH[c] | 7.27 | 7.24 | 7.50 |
| Droplet size (nm)[d] | 15-16 | 16-17 | 300-400 |
| Poly Dispersion Index (PDI)[d] | 0.079 | 0.043 | 0.222 |
| Osmolality (mOsm/Kg)[e] | 389 | 302 | 333.5 |
| Surface Tension (mM/m) | 32.208 | 33.358 | NA |

[a]Microscopy analysis: Nikon Eclipse 80i
[b]Turbidity evaluation: HI 83414 Turbidity and free/Total Chlorine Meter by HANNA instruments (using calibration curve samples and WFI of 0.13 NTU as reference)
[c]pH measurements: SevenEasy Mettler Toledo
[d]Drop size examination: Zeta sizer, nano sizer (nano-s), MALVERN instrument
[e]Fiske ® Micro-Osmometer (model 210)

TABLE 3-2

Properties of B10 and B11 based microemulsions compared to CLE

| Parameter | Microemulsion prepared from propofol concentrate | | |
|---|---|---|---|
| | B10A | B11A | CLE |
| Transparency | Yes | Yes | No |
| Color | Clear yellowish | Clear yellowish | White opaque |
| Microscopy | Uniform | Uniform | Uniform |
| Turbidity (NTU) | 45.3 | 61.7 | NA |
| Droplet size (nm) | 18-19 | 19-20 | 300-400 |
| Poly Dispersion Index (PDI) | 0.051 | 0.085 | 0.222 |

As clearly shown in Tables 3-1 and 3-2, B6A, B9A, B10A and B11A microemulsions have significantly different properties from those of commercial emulsions (CLE).

Commercial emulsions are typically a dispersion of two immiscible liquids, formed in the presence of emulsifiers/surfactants, which reduce the interfacial tension between the two phases and cover the dispersed droplets to retard aggregation, flocculation, coalescence and phase separation. Since the emulsifiers do not reduce the interfacial tension to zero and the coverage is not complete, emulsions require application of relatively high shear forces of multistage homogenizer to reduce the droplets size upon preparation of the emulsion. The resulting non-uniform droplets have a strong tendency to coalesce and/or result in phase separation, thereby stabilizing the system energetically. Thus, commercial propofol emulsions show a relatively non-uniform and large droplet size, which are unstable over prolonged periods of time (i.e. the droplet size increases due to coalescence or can even result in phase separation). Moreover, the CLE droplet size is far from being homogenous (as evident from the relatively high polydispersity index), also resulting in a milky, white-opaque appearance.

Contrary to CLE, due to the zero interfacial tension, microemulsions of the invention, such as B6A and B9A microemulsions are spontaneously formed as energetically balanced systems, which are characterized by a small and uniform droplet size, resulting in transparent systems.

Similar microemulsions formulations in which glycerol was used instead of polyethylene glycol as a co-surfactant are provided in Table 4-1.

TABLE 4-1

Propofol-microemulsions, 1 wt % propofol

| | Solutol | PG | MCT | PEG 400 | Ethanol | PC** | Glycerol | Propofol | Water |
|---|---|---|---|---|---|---|---|---|---|
| F(I) | 7.556 | 0.229 | 0.707 | 0 | 0.556 | 0.202 | 0.859 | 1 | 89.891 |
| F(II) | 7.556 | 0.229 | 0.707 | 0.859 | 0.556 | 0.202 | 0 | 1 | 89.891 |

*All quantities in wt %
**phosphatidyl-choline

Further suitable microemulsions were obtained when replacing Solutol HS15 with Tween 80, as shown in Table 4-2.

TABLE 4-2

Propofol-microemulsions, 1 wt % propofol

| | Tween 80 | PG | MCT | Ethanol | PC** | Glycerol | Propofol | Water |
|---|---|---|---|---|---|---|---|---|
| F(III) | 8.593 | 0.261 | 0.805 | 0.632 | 0.23 | 0.977 | 1 | 87.502 |
| F(IV) | 7.578 | 0.409 | 0.675 | 0.675 | 0 | 0.772 | 1 | 89.891 |

*All quantities in wt %
**phosphatidyl-choline

Example II: Propofol-Microemulsions Compared to Shear-Mixed Emulsions

Due to the poor solubility of propofol, the majority of propofol emulsions currently under research are produced by utilizing high-shear forces. It is important to note that although such emulsions are often inappropriately named "microemulsions" or "nanoemulsions" in literature (see, for example [1]), such emulsions are significantly different from those of the present invention.

In order to demonstrate the differences between shear-mixed emulsions and microemulsions of the present invention, the following comparative example was carried out.
Shear Mixed Emulsion
Example 1 in [1] was selected as a representative example of a typical shear-mixed emulsion.

Unloaded Shear-Mixed Emulsion (without Propofol)

785 mg Labrafac™ CC (caprylic/capric triglyceride) and 527 mg Macrogol 15 hydroxystearate (also known as Solutol HS15) were precisely weighted into 20 ml glass vial. The mixture was heated to 40° C. for 15 minutes under agitation at 630 rpm and then cooled down to room temperature for 5 minutes.

A dispersing phase (0.9% w/v NaCl in water, i.e. physiological saline) was added to the mixture under agitation at 630 rpm until a final volume of 15 ml was obtained. The formulation was heated and mixed at 40° C. for an additional 10 minutes at 840 rpm. At this stage, prior to application of shear forces, the diameter of the droplets and PDI of the premix was determined by dynamic light scattering (Malvern Instrument, MAL500572, model ZEN1600).

The premix was then homogenized with a high-pressure homogenizer (IKA Labortechnik, Type T25B) at 10,000 psi for 105 seconds. After homogenization, the mean droplet diameter and PDI was measured again.

Propofol-Loaded Shear-Mixed Emulsion (1 wt %)

785 mg Labrafac™ CC and 527 mg Macrogol 15 hydroxystearate were precisely weighted into 20 ml glass vial. The mixture was heated to 40° C. for 15 minutes under agitation at 630 rpm and then cooled down to room temperature for 5 minutes.

150 mg of propofol was added to the mixture and mixed at 630 rpm for 5 minutes.

A dispersing phase (0.9% w/v NaCl in water, i.e. physiological saline) was added to the mixture under agitation at 630 rpm until a final volume of 15 ml was obtained. The formulation was heated and mixed at 40° C. for an additional 10 minutes at 840 rpm. At this stage, prior to application of shear forces the diameter of the droplets and PDI of the mixture was determined by dynamic light scattering (Malvern Instrument, MAL500572, model ZEN1600).

The mixture was then homogenized with a high-pressure homogenizer (IKA Labortechnik, Type T25B) at 10,000 psi for 105 seconds. After homogenization, the mean droplet diameter and PDI was measured again.

Unloaded and Loaded Propofol Microemulsions

B6A and B9A propofol microemulsions (prepared from B6 and B9 concentrates) were prepared according to Example I above. Similar unloaded microemulsions were also prepared (i.e. maintaining the same components ratio, however without addition of propofol).

Average droplet size and PDI values for all samples are shown in Table 5.

TABLE 5

Average droplet size and PDI values

| Formulation | Homogenization | Droplet size (nm) | PDI |
| --- | --- | --- | --- |
| Unloaded shear-mixed emulsion (Example 1 from [1]) | No | 196 | 0.126 |
|  | Yes | 166.2 | 0.1613 |
| 1 wt % propofol shear-mixed emulsion (Example 1 from [1]) | No | 267.5 | 0.183 |
|  | Yes | 27.9, 97.1, 320.3 | 0.396 |
| B6A unloaded microemulsion | No | 13.02 | 0.091 |
| B6A 1 wt % propofol microemulsion | No | 15.29 | 0.084 |
| B9A unloaded microemulsion | No | 13.01 | 0.035 |
| B9A 1 wt % propofol microemulsion | No | 16.29 | 0.049 |

As can clearly be seen, contrary to the small and uniform droplet size spontaneously obtained (without homogenization) for B6A and B9A propofol-microemulsions, the shear-mixed emulsions show a significantly larger droplet size (about an order of magnitude larger) prior to high-pressure homogenization. Moreover, after shearing the emulsions by employing a high-pressure homogenization, the emulsions' droplet size does not decrease significantly, and for the propofol-loaded emulsion a three-population distribution of droplet sizes was observed. Namely, the shear-mixed 1 wt % propofol emulsion is far from being mono-dispersed.

Figure 1B:
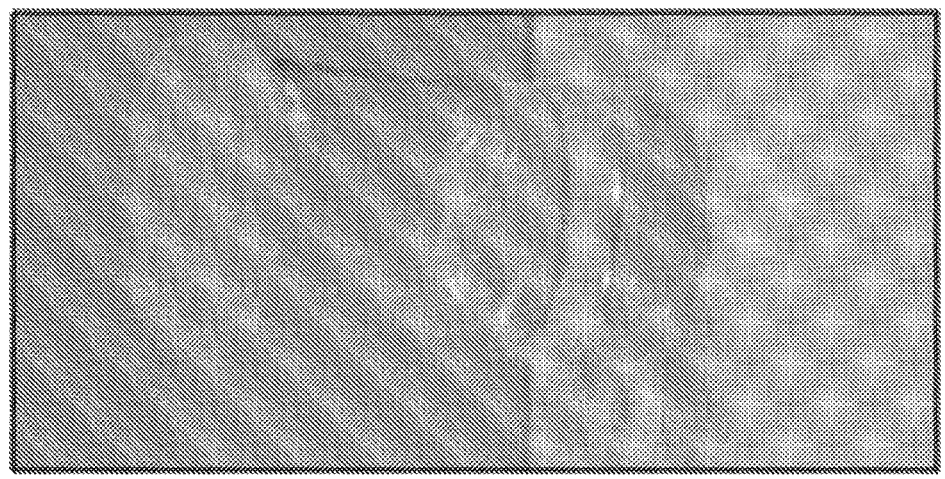
Figure 1C:

This is also supported by the appearance of the samples. As can clearly be seen in FIG. 1C, the relatively large and inhomogeneous droplet size of the shear-mixed emulsion is milky in appearance, compared to the clear and transparent microemulsion (FIGS. 1A-1B).

Example III: Dilutablity of Propofol-Microemulsions

One of the advantages of propofol-concentrated of the invention (such as B9) is the ability to dilute them at various dilution ratios, without significantly affecting their droplet size.

Figure 2A:
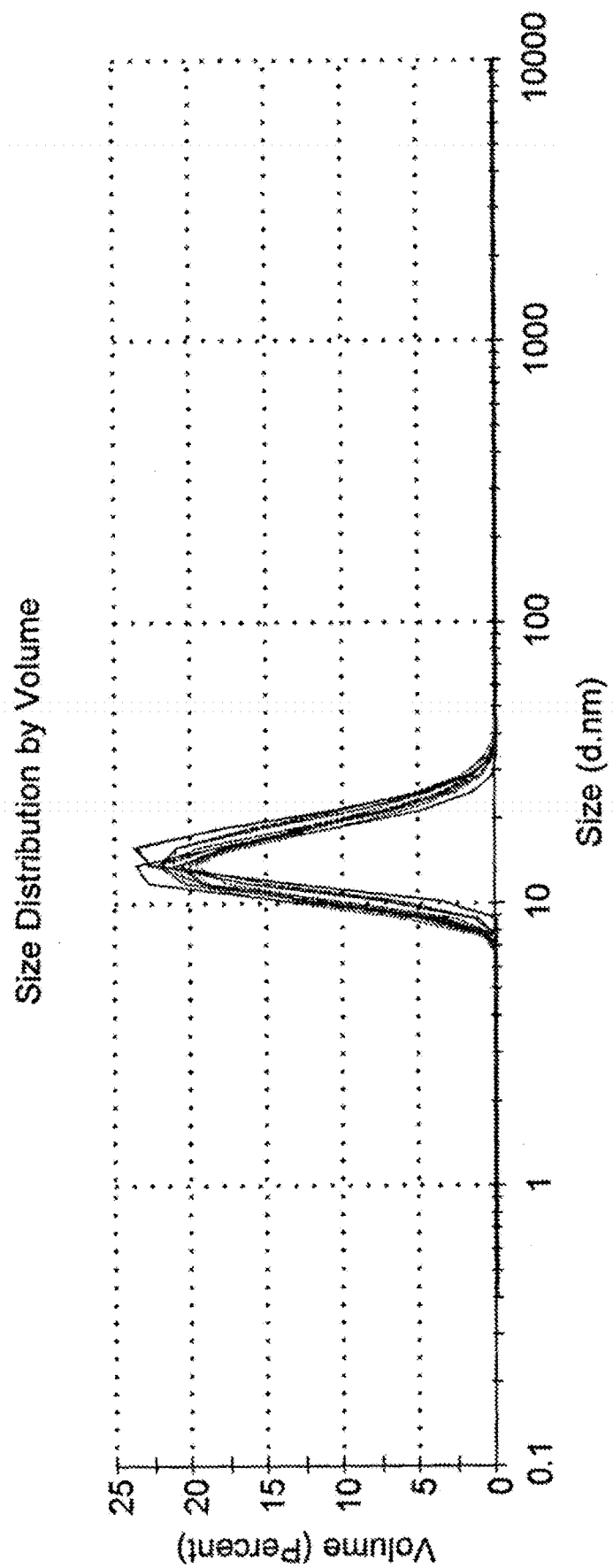
FIG. 2A shows droplet size distribution, as measured by DLS (Dynamic Light Scattering) analysis for a microemulsion prepared by diluting a 6 wt % propofol concentrate by water for injection; water concentration in the microemulsion ranging from 83.33 to 95 wt %.
Figure 2B:
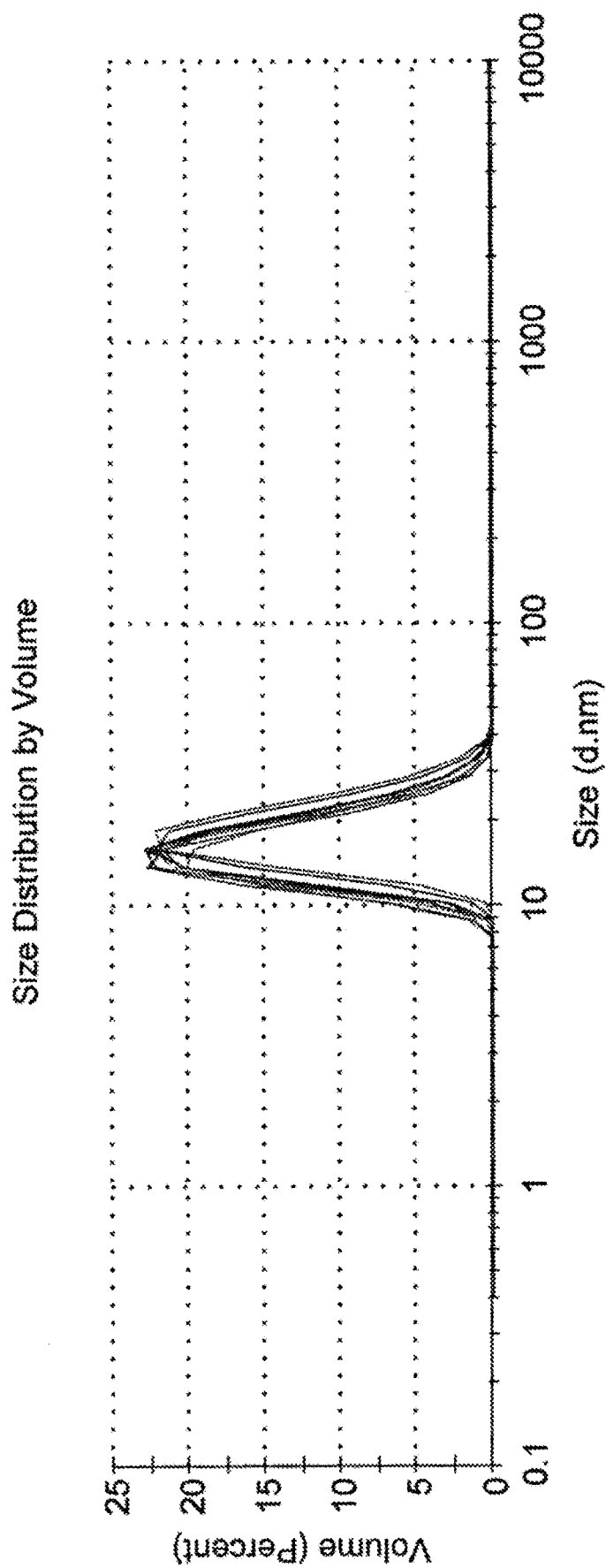
FIG. 2B shows droplets size distribution, as measured by DLS for a microemulsion prepared by diluting a 9 wt % propofol concentrate by water for injection; water concentration in the microemulsion ranging from 88.88 to 95 wt %.
Figure 2C:
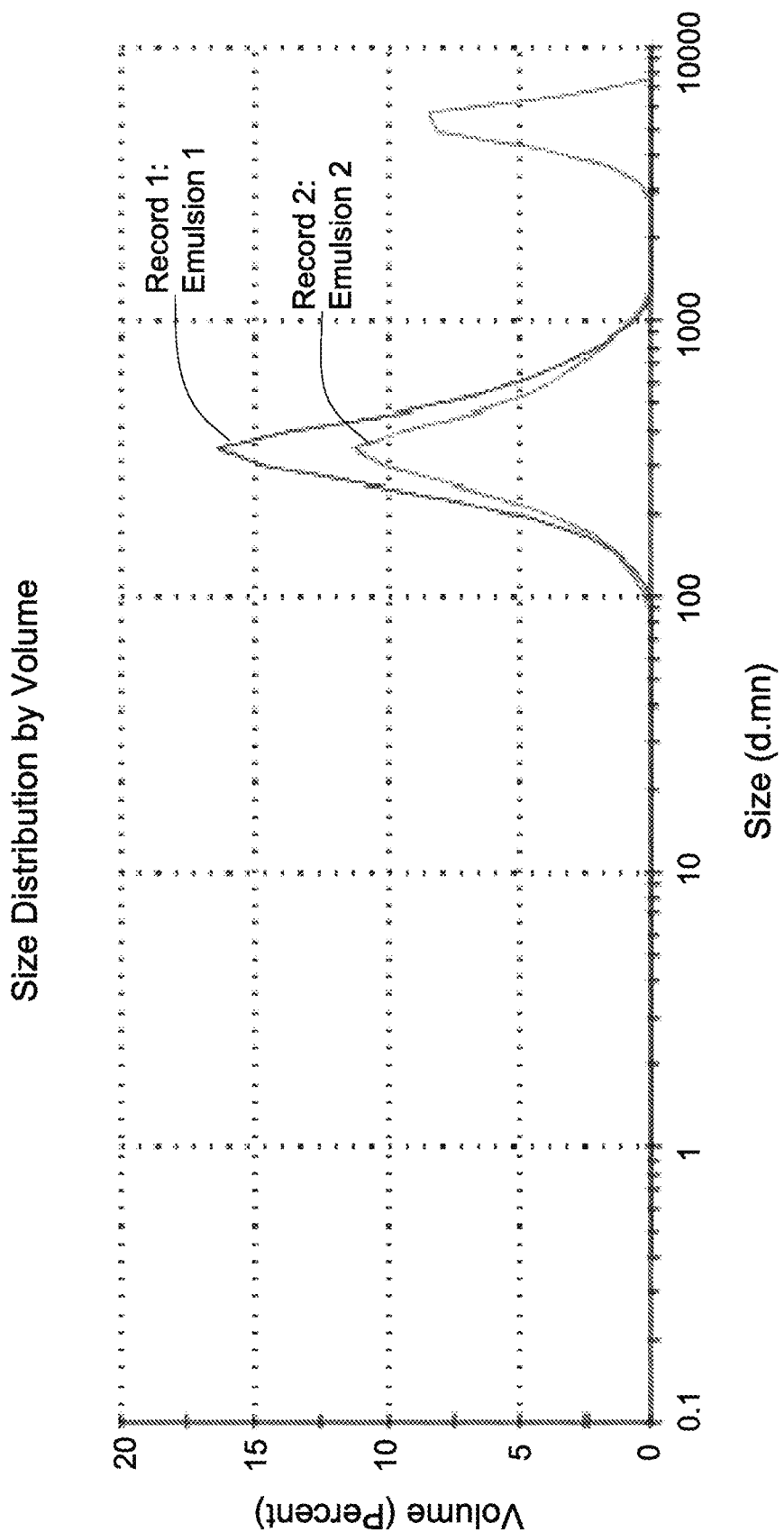
FIG. 2C shows droplets size distribution, as measured by DLS for CLE (Commercial Lipid Emulsion, Propofol-Lipuro®).
Figure 3A:
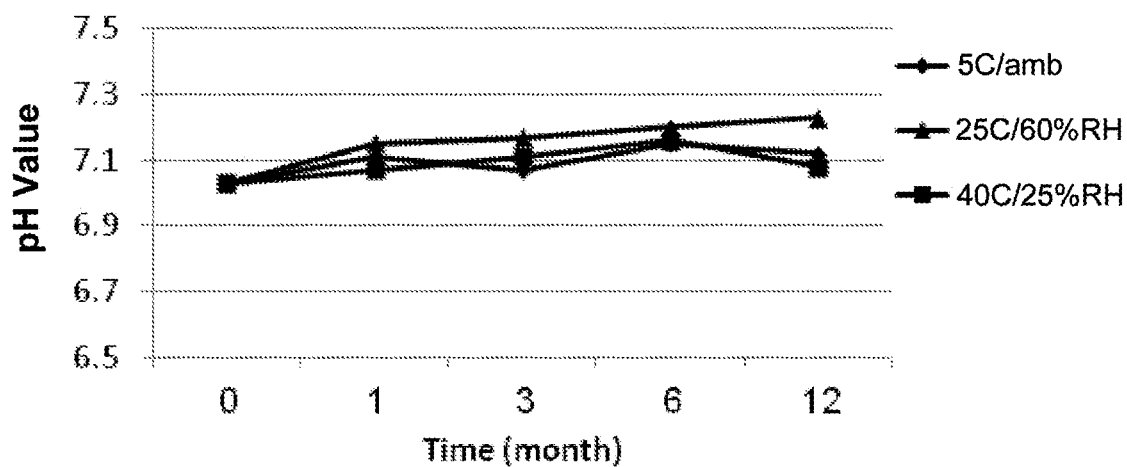
FIGS. 3A-3B show pH changes in accelerated stability studies of B6- (FIG. 3A) and B9-based (FIG. 3B) diluted formulations.
Figure 3B:
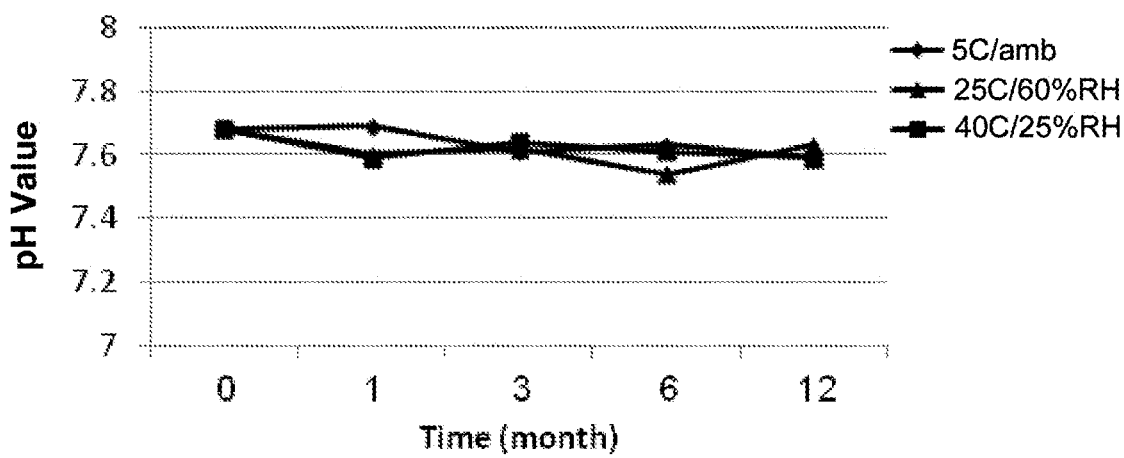
Figure 4A:
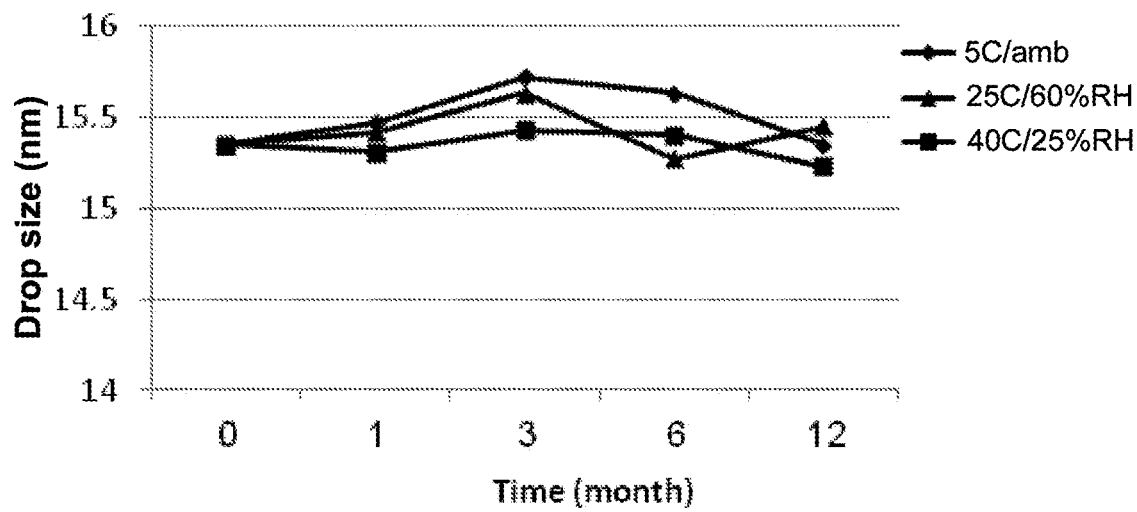
FIGS. 4A-4B show droplet size changes in accelerated stability studies of B6-(FIG. 4A) and B9-based (FIG. 4B) diluted formulations.
Figure 4B:
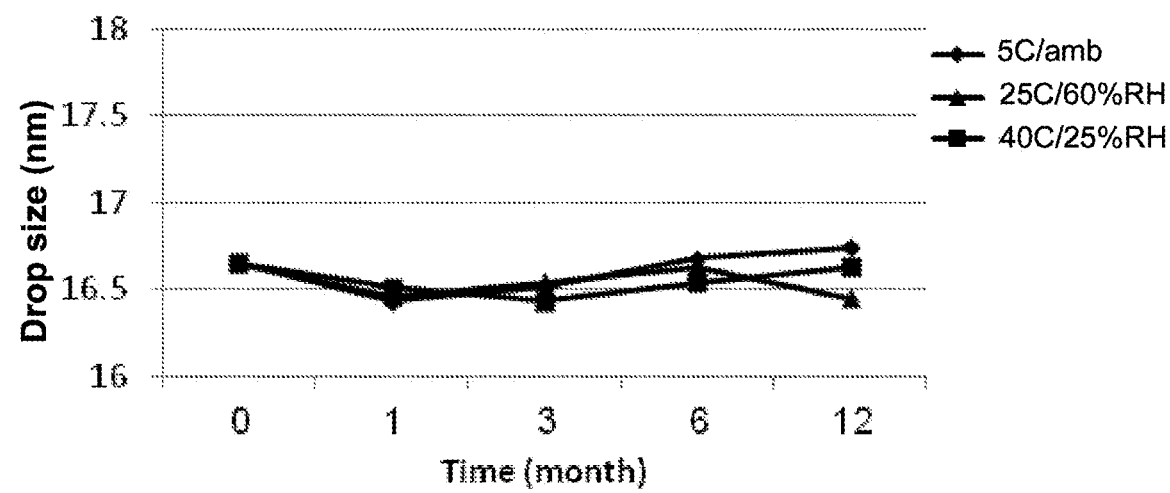
Figures 5A, 5B, 5C, 5D:
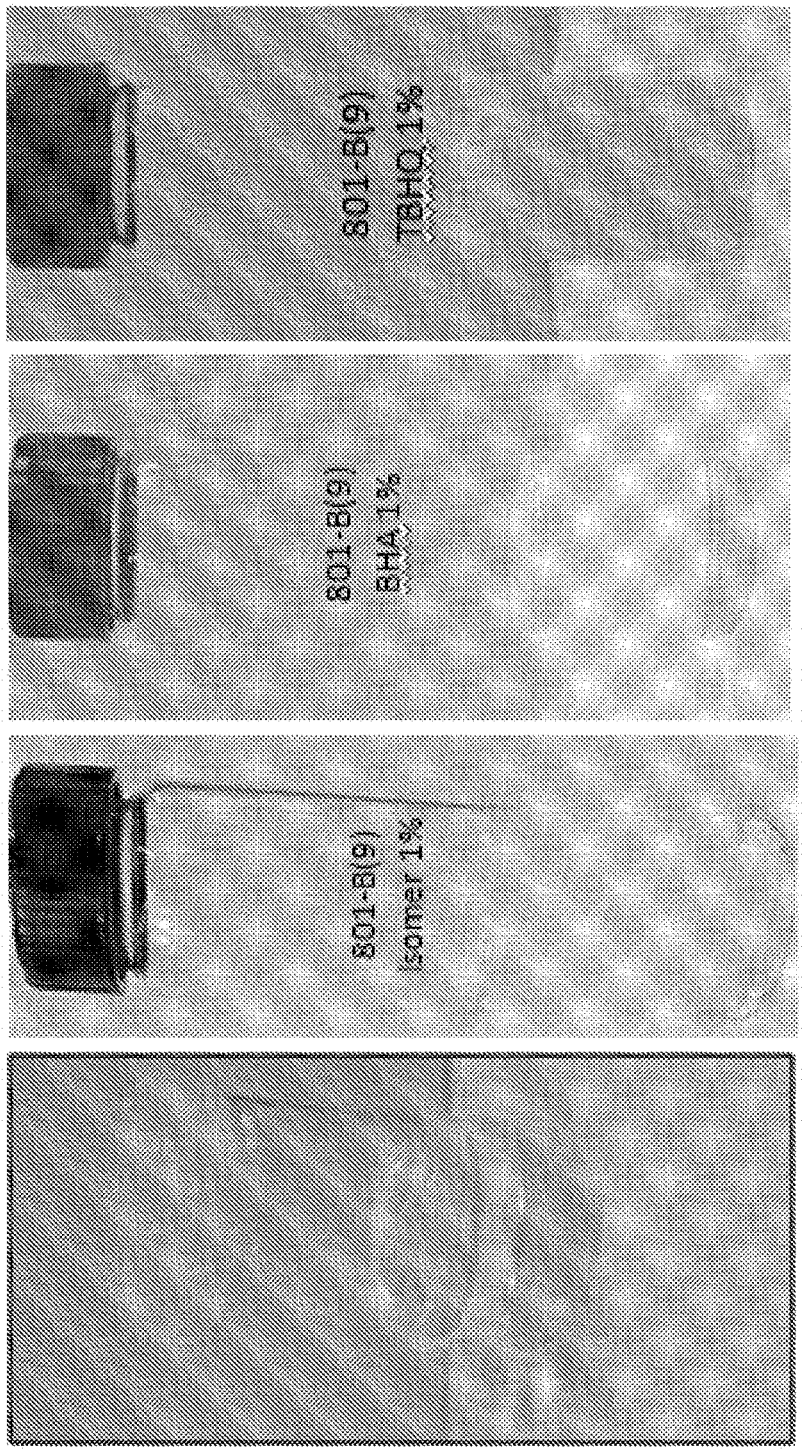
FIGS. 5A-5D shows microemulsions loaded with 1 wt % of propofol (FIG. 5A), 2,4-isomer of propofol (FIG. 5B), BHA (FIG. 5C), and TBHQ (FIG. 5D).

The hydrodynamic radius of the microemulsion droplets were measured at room temperature by dynamic light scattering (DLS) using Nano-ZS Zetasizer (Malvern, UK), with water as a dispersant. The samples were examined in polystyrene disposable cuvettes. For each set of tests, the starting point was a 1 wt % propofol microemulsion, which was further diluted to obtain the samples (as listed in the table below). Average droplet size and PDI values are provided in Table 6. Size distribution curves are presented in FIGS. 2A-2B, as compared to those of commercial propofol emulsions (propofol Lipuro®) in FIG. 2C.

TABLE 6

Average droplet size and PDI values at different dilutions

| Test series | Sample | wt % Water | Size (nm) | PDI |
| --- | --- | --- | --- | --- |
| B6-based microemulsion | 1 | 83.33* | 15.29 | 0.084 |
|  | 2 | 90 | 14.72 | 0.072 |
|  | 3 | 92 | 14.9 | 0.043 |
|  | 4 | 96 | 14.6 | 0.062 |
|  | 5 | 98 | 14.15 | 0.073 |
| B9-based microemulsion | 1 | 88.88* | 16.76 | 0.049 |
|  | 2 | 90 | 16.72 | 0.061 |
|  | 3 | 92 | 16.76 | 0.047 |
|  | 4 | 96 | 16.29 | 0.04 |
|  | 5 | 98 | 16.02 | 0.032 |
| CLE |  |  | N/A |  |

*1 wt % propofol microemulsion

As clearly evident from Table 6, the droplet sizes of the empty system are smaller than those measured for the loaded systems indicating that Propofol is located within the core/interface of the drop increasing its size (see also SD-NMR analysis in Example V below).

When compared to commercial propofol emulsions, it can be further observed that the propofol-microemulsions of the invention are fully dilutable without significantly altering the droplet size.

Note that comparative results for dilution of CLE cannot be obtained, as dilution of the CLE caused phase separation. In a typical experiment temperature fluctuation between 20-40° C. showed an increase of more than 20% in droplets sizes and additional storage at 40° c. showed the beginning of coalescence phenomenon that leads to phase separation after 60 days as shown in Table 7.

This suggests that propofol-microemulsions allow better control of propofol dosing, giving the care taker the possibility to further dilute the microemulsion to a desired lower concentration of propofol, without changing the microemulsion's physical structure and maintaining its beneficial properties. This is of significance, as once introduced into the bloodstream, microemulsions of the invention will not coalesce and/or form aggregates (unlike commercial emulsions).

Example IV: Long-Term Physical Stability

The stability of the propofol-microemulsion B6A and B9A, loaded with 10 mg/ml propofol (1 wt %), was evaluated for a period of 12 months, at three different temperatures and relative humidity (% RH) conditions (5° C./ambient, 25° C./60% RH and 40° C./25% RH).

Clarity, pH and droplet size was measured at each time point at triplicate samples, and compared to the initial measurements (baseline at time 0) taken immediately after preparation of the formulations. The results are presented in Tables 7-9 and FIGS. 3A-4B.

TABLE 7

CLE stability over time

| Temperature of storage (° C.) | Time (months) | pH | # of globules >2 μm |
|---|---|---|---|
| 30 | 0 | 8.4 | 253 |
|  | 6 | 7.6 | 476 |
|  | 12 | 7.3 | 661 |
| 40 | 0 | 8.4 | 253 |
|  | 6 | 7.0 | 987 |
|  | 12 | 6.1 | 1527 |

TABLE 8

Stability analysis for B6A formulation (10 mg/ml propofol)

| Storage Conditions | Time (months) | Clarity | pH | Droplet Size (nm) | PDI |
|---|---|---|---|---|---|
| Initial | 0 | ✓ | 7.03 | 15.35 | 0.044 |
| 5° C. | 1 | ✓ | 7.11 | 15.27 | 0.046 |
| Ambient | 3 | ✓ | 7.07 | 15.72 | 0.042 |
| humidity | 6 | ✓ | 7.15 | 15.63 | 0.050 |
|  | 12 | ✓ | 7.12 | 15.35 | 0.043 |
| 25° C. | 1 | ✓ | 7.01 | 15.42 | 0.046 |
| 60% RHA | 3 | ✓ | 7.17 | 15.73 | 0.049 |
|  | 6 | ✓ | 7.20 | 15.27 | 0.051 |
|  | 12 | ✓ | 7.23 | 15.45 | 0.061 |
| 40° C. | 1 | ✓ | 6.99 | 15.31 | 0.054 |
| 25% RHA | 3 | ✓ | 7.01 | 15.63 | 0.047 |
|  | 6 | ✓ | 7.16 | 15.40 | 0.049 |
|  | 12 | ✓ | 7.03 | 15.23 | 0.050 |

TABLE 9

Stability analysis for B9A formulation (10 mg/ml propofol)

| Storage Conditions | Time (months) | Clarity | pH | Droplet Size (nm) | PDI |
|---|---|---|---|---|---|
| Initial | 0 | ✓ | 7.68 | 16.65 | 0.057 |
| 5° C. | 1 | ✓ | 7.69 | 16.07 | 0.064 |
| Ambient | 3 | ✓ | 7.61 | 16.23 | 0.072 |

TABLE 9-continued

Stability analysis for B9A formulation (10 mg/ml propofol)

| Storage Conditions | Time (months) | Clarity | pH | Droplet Size (nm) | PDI |
|---|---|---|---|---|---|
| humidity | 6 | ✓ | 7.63 | 16.77 | 0.053 |
|  | 12 | ✓ | 7.59 | 16.32 | 0.043 |
| 25° C. | 1 | ✓ | 7.60 | 16.46 | 0.059 |
| 60% RHA | 3 | ✓ | 7.62 | 16.54 | 0.049 |
|  | 6 | ✓ | 7.54 | 16.63 | 0.047 |
|  | 12 | ✓ | 7.63 | 16.45 | 0.059 |
| 40° C. | 1 | ✓ | 7.59 | 16.51 | 0.061 |
| 25% RHA | 3 | ✓ | 7.64 | 16.43 | 0.043 |
|  | 6 | ✓ | 7.61 | 16.54 | 0.053 |
|  | 12 | ✓ | 7.59 | 16.63 | 0.042 |

As can be observed, the microemulsions maintain their clarity, pH, droplet size and PDI values over prolonged periods of time, i.e. at least up to 12 months, when stored at various storage conditions. Thus, diluted formulations of the invention may be stored for prolonged periods of time without adversely affecting their properties.

It is known from the literature that an emulsion's stability is derived from several kinetics forces: the formation of mechanical barrier between the oil and the aqueous phases and electrostatic repulsive forces between the droplets. These forces tend to be disrupted causing the emulsion to degrade and separate to the oil and water phases. Moreover, during heat sterilization of the emulsion, small quantities of free fatty acids and hydrolysis of the soybean oil leads to pH decrease, which in turn act to destabilize the emulsion. This process continues even during storage, since the emulsions are non-buffered. Therefore, propofol commercial emulsions have a relatively narrow expiration date, of two years, with specific storage condition (see Table 7).

To determine long term stability of formulations, a rapid measurement was carried out using LUMiFuge™ analytical centrifugation. LUMiFuge analysis enables to predict the shelf-life of a formulation in its original concentration, even in cases of slow destabilization processes like sedimentation, flocculation, coalescence and fractionation. During LUMiFuge measurements, parallel light illuminates the entire sample cell in a centrifugal field; the transmitted light is detected by sensors arranged linearly along the total length of the sample-cell. Local alterations of particles or droplets are detected due to changes in light transmission over time. The results are presented in a graph plotting the percentage of transmitted light (Transmission %) as a function of local position (mm), revealing the corresponding transmission profile over time. The commercial propofol emulsion, Propofol-Lipuro®, was compared to measurements carried out on B6- and B9-based formulations over a time period of 24 hours.

The initial detection of the Propofol-Lipuro® lipid-based emulsion (having white milky appearance) scattered and absorbed the light resulting in low transmission (close to 0%). However, within time, the emulsion stability was impaired, leading to phase separation. These results demonstrate the Propofol-Lipuro® emulsion instability concern, which might be harmful and even lethal to patients going anesthetic procedures and administered with the lipid-based emulsion.

In contrast, in microemulsions of the invention (having a clear and transparent appearance) enabled light to be transmitted (100%) throughout the whole measured cell length. The transmitted light, reflecting the transparency of the sample, was even obtained over 24 hours of centrifugal forces of 3000 rpm tested during analysis. The LUMiFuge recorded transmission for the microemulsion was similar to those measured for water. These results support expectation for long shelf life stability properties of the tested microemulsions and the safety profile of such formulations used in patient even after long storage occasion. Thus, microemulsions of the invention are thermodynamically stable and therefore are expected to have broader storage conditions with less requirements for proper storage. The ability to store the microemulsion in higher and lower temperature, as well as longer time-periods, is an important advantage in the pharmaceutical industry.

Example V: Self-Diffusion NMR (SD-NMR)

In order to determine the structure of the oil droplets (or micelles) of the microemulsions, self-diffusion NMR analysis was carried out. SD-NMR is able to locate each component within the microemulsion via measurements of its diffusion coefficient. Rapid diffusion ($>100\times10^{-11}$ $m^2s^{-1}$) is characteristic of small molecules, free in solution, while slow diffusion coefficients ($<0.1\times10^{-11}$ $m^2s^{-1}$) suggest low mobility of macromolecules or bound/aggregated molecules.

NMR measurements were performed with a Bruker AVII 500 spectrometer equipped with GREAT 1/10 gradients, a 5 mm BBO and a 5 mm BBI probe, both with a z-gradient coil and with a maximum gradient strength of 0.509 and 0.544 T $m^{-1}$, respectively. Diffusion was measured using an asymmetric bipolar longitudinal eddy-current delay (bpLED) experiment, or and asymmetric bipolar stimulated echo (known as one-shot) experiment with convection compensation and an asymmetry factor of 20%, ramping the strongest gradient from 2% to 95% of maximum strength in 32 steps. The spectrum was processed with the Bruker TOPSPIN software. NMR spectra were recorded at 25±0.2° C. The components were identified by their chemical shift in 1H NMR.

Table 10-1 shows the diffusion coefficients (Dx, $m^2$/sec) of the various components for B6- and B9-based unloaded and 1 wt % propofol-loaded microemulsions.

TABLE 10-1

Diffusion coefficients ($m^2$/sec), as measured by SD-NMR, Solutol as surfactant

| Component | B6A microemulsion | | B9A microemulsion | |
| --- | --- | --- | --- | --- |
| | Unloaded | Loaded | Unloaded | Loaded |
| Water | $1.76 \times 10^{-9}$ | $1.37 \times 10^{-9}$ | $1.52 \times 10^{-9}$ | $1.62 \times 10^{-9}$ |
| Propofol | — | $1.02 \times 10^{-11}$ | — | $1.54 \times 10^{-11}$ |
| Solutol | $1.45 \times 10^{-11}$ | $1.62 \times 10^{-11}$ | $1.94 \times 10^{-11}$ | $1.50 \times 10^{-11}$ |
| Propylene glycol | $6.68 \times 10^{-10}$ | $5.22 \times 10^{-10}$ | $5.96 \times 10^{-10}$ | $8.45 \times 10^{-10}$ |
| Ethanol | $8.83 \times 10^{-10}$ | $6.91 \times 10^{-10}$ | $7.65 \times 10^{-10}$ | $9.82 \times 10^{-10}$ |

*Note:
MCT shows similar diffusion coefficients to propofol, however its low content prevents obtaining accurate calculation of the diffusivity.

As can be seen from Table 10, the diffusion coefficient of Solutol HS15 is similar to that of Propofol. These results indicate that the propofol is located within the core and the interface of the swollen micelle. This suggests that all of the propofol in the tested microemulsions is contained within the oil droplet, and no free propofol is within the aqueous continuous phase. Since free propofol in known to be the cause of pain upon injection, the fact that propofol is located within the oil droplets is expected to significantly reduce pain and irritation during and following administration.

In addition, it should be also stressed that the droplet size is increasing when propofol is introduced into the system compared to the empty system from 12.5 nm to 17 nm. This indicates that propofol resides within the core of the droplet, thereby increasing its diameter.

Similar results were obtained when replacing Solutol HS15 with Tween 60 or Tween 80, as shown in Table 10-2.

TABLE 10-2

Diffusion coefficients ($m^2$/sec), as measured by SD-NMR, Tween as surfactant

| Component | Formulation with Tween 80 | | Formulation with Tween 60 | |
| --- | --- | --- | --- | --- |
| | Unloaded | Loaded | Unloaded | Loaded |
| Water | $1.91 \times 10^{-9}$ | $1.24 \times 10^{-9}$ | $1.86 \times 10^{-9}$ | $1.12 \times 10^{-9}$ |
| Propofol | — | $1.73 \times 10^{-11}$ | — | $1.04 \times 10^{-11}$ |
| Tween | $1.73 \times 10^{-11}$ | $2.08 \times 10^{-11}$ | $0.92 \times 10^{-11}$ | $1.63 \times 10^{-11}$ |
| Propylene glycol | $5.43 \times 10^{-10}$ | $4.82 \times 10^{-10}$ | $4.96 \times 10^{-10}$ | $3.24 \times 10^{-10}$ |

It was also found that when the surfactant was replaced by a surfactant (such as sucrose ester) that does not have a diffusion coefficient similar to that of the propofol in the microemulsion, no stable microemulsion was formed. As propofol moved somewhat faster, binding between propofol and an unsuitable surfactant is less strong, and hence more of the propofol is in free form in the aqueous phase. This may suggest that incorporation of propofol in other microemulsion composition results in deviation from equilibrium and formation non-stable microemulsions, or such that cannot be fully diluted.

The relationship between the surfactant and the propofol with respect to binding in the microemulsion-composition was assessed by loading B9A with 1 wt % of species similar in their structure to propofol. The results are provided in Table 11.

TABLE 11
Diffusion coefficients (m²/sec), as measured by SD-NMR, for various compounds
| Loaded-specie | Loaded specie | Solutol | PEG400 | PG | EtOH |
|---|---|---|---|---|---|
| Empty System | — | 1.94 | 26.3 | 76.5 | 99.8 |
| Propofol 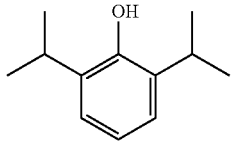 | 1.54 | 1.50 | 26.3 | 84.5 | 98.2 |
| Aniline 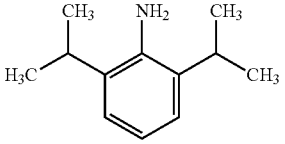 | 2.15 | 1.76 | 26.2 | 44.8 | 94.6 |
| 2,4-isomer 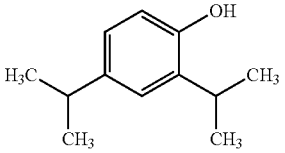 | 1.75 | 1.63 | 26.3 | 73.6 | 96.6 |
| BHA (2-tertbutyl-4-hydroxyanisole) 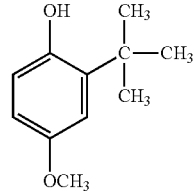 | 1.78 | 1.75 | 24.5 | 78.3 | 91.2 |
| BHA (2,6-Bis(1,1-dimethylethyl)-4-methylphenol) 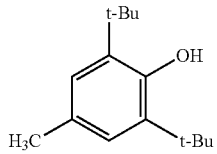 | 1.58 | 1.75 | 24.3 | 79.1 | 98.2 |
| 2-(1,1-dimethylethyl)-1,4-benzendiol (TBHQ) 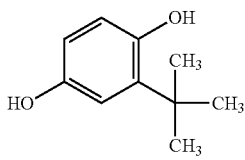 | NA | NA | NA | NA | NA |
(Diffusion coefficient $\times 10^{-11}$)

As can be seen from Table 11, diffusion coefficients of the propofol and the Solutol are almost identical, attesting to the binding between propofol and Solutol in the microemulsion composition, and the presence of the majority (if not all) of the propofol within the oil core or solubilized within the tails of the surfactant.

Although some of the examined species tested show similarity of diffusion coefficient to that of Solutol (such as the 2,4-isomer, BHA and BHT), as evident from FIGS. 5A-5D, such formulations are far from being sufficiently solubilized in the oil phase, resulting in systems which are not completely transparent. In some cases similar structures to propofol, such as TBHQ, form a classic milky emulsion.

These results attest to the uniqueness of the microemulsion formulation composition to the location of propofol within the droplets in which the diffusion coefficients are of the same order of magnitude.

Example VI: In Vitro Hemolysis

10 μl of diluted formulation of B9 or B6 (i.e. B6A and B9A microemulsions) were placed on Trypticase soy agar plates with 5% defibrinated sheep blood (TSA 5% DSB) and incubated up to 24 hours.

Two formulations were used as control: 10 μl of Triton X100, known to cause blood hemolysis, was applied on one third of the plate, and 10 μl of 0.9% NaCl which does not cause hemolysis, was spread on the remaining third.

Figure 6A:
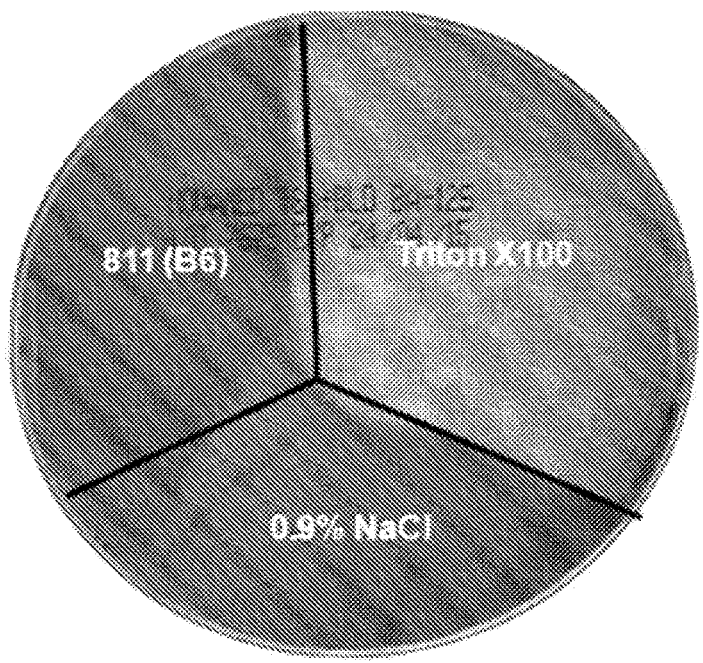
FIGS. 6A-6B shows hemolysis test results for B6A (FIG. 6A) and B9A (FIG. 6B) diluted propofol microemulsion placed on blood agar plates, compared with positive control causing hemolysis of Triton X100 and 0.9% saline, a negative control that do not cause hemolysis.
Figure 6B:
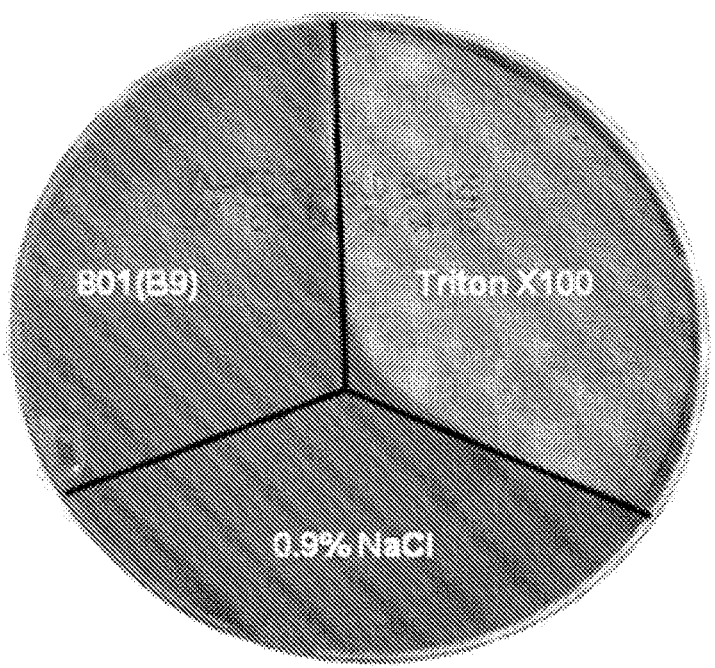

Both formulations tested showed no blood hemolysis, similarly to physiological saline (0.9% NaCl)—see FIGS. 6A-6B.

Example VII: Microorganisms Growth Contamination

Cultures of *S. aureus, E. coli, P. aeruginosa* and *C. albicans* were freshly prepared on the day before the assay (Soybean-casein digest agar for bacteria and Sabouraud dextrose agar for *C. albicans*) from frozen stocks of P2 (after two passages from the original ATCC cultures). Single colonies were picked and suspended in 0.9% sterile saline at a final density of $1.0 \times 10^8$ CFU/ml.

B6A and B9A microemulsions (1% propofol) were aliquoted into five portions (4 gram each) in capped bacteriological test tubes in aseptic conditions to assure avoiding sample contamination. Aliquots of 0.04 ml (i.e., 1% of the volume of test article) of bacterial and fungal suspensions and saline (serving as negative control for contamination of the original formulations) were then added to each test tube to give a starting density of $\sim 1.0 \times 10^6$ CFU/ml. The resulting mixtures were vortexed thoroughly.

Similar aliquots were obtained for CLE.

As a positive control, 0.04 ml aliquots of bacterial and fungal suspensions were added to 4 ml of sterile saline. All controls were subjected to the same testing processes as the test articles.

Aliquots of 0.5 ml were removed from each tube (i.e., $T_0$ sample—in practice all the samples were removed within 30 min after mixing, $T_{0.5}$ is used to reflect this). For each sample, three 0.1 ml aliquots of $T_{0.5}$ mixture (without dilution) were spread on three appropriate solid agar plates. The remaining mixture was diluted 100, 1,000 and 10,000 times, and three aliquots of 0.1 ml were spread on three agar plates. For the CLE, duplicates of 0.1 ml of samples were spread on plated without dilution, 1,000 and 10,000 times diluted (see Table 11-1). The resulting bacterial plates were kept at 37° C. and 85% humidity for 24 hours, and the fungal plate was kept at room temperature for 48 hours. The CFUs were then enumerated and converted to the CFU/ml of the starting materials.

The mixtures were kept at 25° C. (with bacterial inocula) or room temperature (with fungal inoculum) without shaking. After 24 hour growth ($T_{24}$ samples), aliquots of 0.5 ml were removed from each test tube. Three aliquots of 0.1 ml (without dilution) were spread on three appropriate agar plates. The undiluted and 100, 1,000 and 10,000 times diluted aliquots were also plated on three appropriate agar plates. For the CLE, duplicates of 0.1 ml of samples were spread on plated with dilution of 1,000, 10,000 and 100,000 times (Table 12-1), and the resulting CFUs were enumerated. The mixtures were returned to incubation for additional 24 hours at the same conditions.

Colony forming units were counted and the CFU/ml was calculated from each dilution. The mean CFU/ml of all dilutions was calculated; the Microbial Migration Rate (MGR) was calculated by dividing the log ratio of CFU/ml after 24 hours incubation to that measured at $T_0$ as follows:

$$\text{MGR} = \text{Log}[(T_{24}\ \text{CFU/ml})/(T_0\ \text{CFU/ml})].$$

The results are provided in Tables 12-2 and 12-3.

TABLE 12-1

Samples for colony forming activities

| | Inocula | S. aureus* | E. coli* | P. aeruginosa* | C. albicans* | Saline**** |
|---|---|---|---|---|---|---|
| Microem. Formulation | B6A (1%)** | $T_{0.5}$ (12 plates)$^a$ | $T_{0.5}$ (12 plates)$^a$ | $T_{0.5}$ (12 plates)$^a$ | $T_{0.5}$ (12 plates)$^a$ | $T_{0.5}$ (2 plates)$^d$ |
| | | $T_{24}$ (12 plates)$^a$ | $T_{24}$ (12 plates)$^a$ | $T_{24}$ (12 plates)$^a$ | $T_{24}$ (12 plates)$^a$ | $T_{0.5}$ (2 plates)$^d$ |
| | | $T_{48}$ (12 plates)$^a$ | $T_{48}$ (12 plates)$^a$ | $T_{48}$ (12 plates)$^a$ | $T_{48}$ (12 plates)$^a$ | $T_{48}$ (2 plates)$^d$ |
| | B9A (1%)** | $T_{0.5}$ (12 plates)$^a$ | $T_{0.5}$ (12 plates)$^a$ | $T_{0.5}$ (12 plates)$^a$ | $T_{0.5}$ (12 plates)$^a$ | $T_{0.5}$ (2 plates)$^d$ |
| | | $T_{24}$ (12 plates)$^a$ | $T_{24}$ (12 plates)$^a$ | $T_{24}$ (12 plates)$^a$ | $T_{24}$ (12 plates)$^a$ | $T_{0.5}$ (2 plates)$^d$ |
| | | $T_{48}$ (12 plates)$^a$ | $T_{48}$ (12 plates)$^a$ | $T_{48}$ (12 plates)$^a$ | $T_{48}$ (12 plates)$^a$ | $T_{48}$ (2 plates)$^d$ |
| | CLE** | $T_{0.5}$ (8 plates)$^b$ | $T_{0.5}$ (8 plates)$^b$ | $T_{0.5}$ (8 plates)$^b$ | $T_{0.5}$ (8 plates)$^b$ | $T_{0.5}$ (2 plates)$^d$ |
| | | $T_{24}$ (8 plates)$^b$ | $T_{24}$ (8 plates)$^b$ | $T_{24}$ (8 plates)$^b$ | $T_{24}$ (8 plates)$^b$ | $T_{0.5}$ (2 plates)$^d$ |
| | | $T_{48}$ (8 plates)$^b$ | $T_{48}$ (8 plates)$^b$ | $T_{48}$ (8 plates)$^b$ | $T_{48}$ (8 plates)$^b$ | $T_{48}$ (2 plates)$^d$ |

TABLE 12-1-continued

| | Samples for colony forming activities | | | | |
|---|---|---|---|---|---|
| Inocula | S. aureus* | E. coli* | P. aeruginosa* | C. albicans* | Saline**** |
| Saline*** | $T_{0.5}$ (8 plates)$^c$ | $T_{0.5}$ (8 plates)$^c$ | $T_{0.5}$ (8 plates)$^c$ | $T_{0.5}$ (8 plates)$^c$ | $T_{0.5}$ (2 plates)$^d$ |
| | $T_{24}$ (8 plates)$^c$ | $T_{24}$ (8 plates)$^c$ | $T_{24}$ (8 plates)$^c$ | $T_{24}$ (8 plates)$^c$ | $T_{24}$ (2 plates)$^d$ |
| | $T_{48}$ (8 plates)$^c$ | $T_{48}$ (8 plates)$^c$ | $T_{48}$ (8 plates)$^c$ | $T_{48}$ (8 plates)$^c$ | $T_{48}$ (2 plates)$^d$ |

Inoculum/volume *~$1.0 \times 10^8$ CFU/ml, 0.04 ml; 4 gram; *4.0 ml; ****0.04 ml
Dilution schemes:
$^a$undiluted, 1/100, 1/1,000 and 1/10,000 dilutions (0.1 ml each, triplicated);
$^b$undiluted 1/1,000 and 1/10,000 and 1/100,000 dilutions (0.1 ml each, duplicated);
$^c$undiluted, 1/100, 1/1,000 and 1/10,000 dilutions (0.1 ml each, duplicated);
$^d$undiluted (0.1 ml each duplicated)

TABLE 12-2

| | | Mean CFU/ml | | |
|---|---|---|---|---|
| | Sampling | Mean CFU/ml ($\times 10^6$) | | |
| Sample | time (hr) | S. aureus | E. coli | P. aeruginosa | C. albicans |
| Saline | 0.5 | 3.75 | 7.53 | 16.63 | 8.90 |
| | 24 | 2.00 | 6.30 | 6.33 | 2.05 |
| B6A | 0.5 | 17.60 | 5.68 | 2.53 | 8.65 |
| | 24 | 19.50 | 0.28 | 0.40 | 2.238 |
| B9A | 0.5 | 17.32 | 2.04 | 0.04 | 9.85 |
| | 24 | 9.58 | 2.07 | 0.01 | 7.87 |
| CLE | 0.5 | 13.23 | 13.53 | 13.50 | 9.85 |
| | 24 | 59.75 | 207.5 | NA | 12.68 |

TABLE 12-3

| Microbial migration rate (MGR) | | | | |
|---|---|---|---|---|
| Sample | S. aureus | E. coli | P. aeruginosa | C. albicans |
| Saline | 0.53 | 0.83 | 0.38 | 0.23 |
| B6A | 1.10 | 0.04 | 0.15 | 0.25 |
| B9A | 0.55 | 1.01 | 0.25 | 0.79 |
| CLE | 4.51 | 15.33 | NA | 1.28 |

Bacterial growth of B6A and B9A formulations decreased or has shown almost no change in growth rate after 24 hours. These results indicate that both formulations do not support microorganism growth. The calculated MGR value of the tested bacterial strains was negative or lower than 0.05. In contrast to the microemulsions, the commercial lipid-based emulsion showed an increase in the growth in all tested microorganisms with an MGR value above 0.5. The MGR calculated value was extremely high (1.19) for the emulsion tested for the growth of E. coli. The results indicate that emulsion provides a good and supportive environment for bacterial and fungal growth, while the microemulsions do not.

Example VIII: Pharmacological Tests

Pharmacokinetics following single intravenous bolus (IV) dose of commercial Propofol-Lipuro® (referred to herein as prototype), and B6A and B9A propofol-containing diluted microemulsions, all with a concentration of 10 mg/ml, was assessed at 6 mg/kg in male beagle dogs. The test article was monitored in plasma up to 8 hours.

Test System and Study Design
Study 1:
3 non-naive male beagle dogs (8.06-9.07 kg, supplied by Marshall Bioresources, Beijing, China) were assigned to the study with 3 males per group. Each animal had a unique skin tattoo number on ear as the identification. The dogs in each group received a single intravenous dose of propofol formulation at a nominal dose of 6 mg/kg. Blood samples were harvested according to each sampling time. The study design is presented in Table 13-1.

Study 2:
18 naive male beagle dogs (7.08-11.16 kg in weight, supplied by Marshall Bioresources, Beijing, China) were assigned to 3 groups with 6 males per group. Each animal had a unique skin tattoo number on ear as the identification. The dogs in each group received a single intravenous dose of propofol formulation at a nominal dose of 6 mg/kg. Blood samples were harvested according to each sampling time. The study design is presented in Table 13-1.

TABLE 13-1

| Pharmacokinetic test design (IV Bolus) | | | | | |
|---|---|---|---|---|---|
| Study # | # of males | Formulation | Dose (mg/kg) | Dose volume (mL/kg) | Dose concentration (mg/mL) |
| 1 | 3 | Prototype | 6 | 0.6 | 10 |
| | 3 | B6Abased | 6 | 0.6 | 10 |
| | 3 | B9Abased | 6 | 0.6 | 10 |
| 2 | 6 | Prototype | 6 | 0.6 | 10 |
| | 6 | B6A | 6 | 0.6 | 10 |
| | 6 | B9A | 6 | 0.6 | 10 |

Dose Preparation and Administration:
Study 1:
B6A and B9A formulations and Prototype were provided as ready to use solutions (in their diluted state, 10 mg/mL). Prior to administration, solution was mixed by slightly shaking the vial, the center disc was opened and the septum rubber cleaned with an alcohol pad. Next, the required volume was retrieved using a sterile syringe going through the septum stopper. Air bubbles were removed before IV injection.
Study 2:
formulations were supplied as concentrated solutions (60 or 90 mg/mL; 6 or 9 wt %) and were diluted to the desired concentration (10 mg/mL) prior to administration. Dose preparation procedure was carried out as follows: water for injection (WFI) was added using a sterile pipette. After the addition of WFI, the cap was closed and the test items was thoroughly mixed by shaking the vial, until a transparent, uniform and clear formulation was formed. The formulation was then left to stand for about 15 min at room temperature to release most bubbles and decrease foam formation. The required volume was retrieved using a sterile syringe, while avoiding taking any foam or bubbles. Each dog out of the six received the required volume-dose from a separate freshly prepared vial. Prototype formulation was supplied as ready to use formulation and was not further diluted prior to administration.

Doses preparations are provided in Table 13-2.

TABLE 13-2

Dose preparation parameters

| Study # | Formulation type | Concentrated dose | Dilution with WFI | Volume after dilution | Number of vials | Total |
|---|---|---|---|---|---|---|
| 1 | Prototype 1% propofol | 20 mL | — | — | 4 | 80 mL (800 mg) |
|  | B6A 1% propofol | 9 mL | — | — | 4 | 36 mL (360 mg) |
|  | B9A 1% propofol | 9 mL | — | — | 4 | 36 mL (360 mg) |
| 2 | Prototype 1% propofol | 20 mL | — | — | 4 | 80 mL (800 mg) |
|  | B6 6% propofol | 1.5 mL | 7.5 mL | 9.0 mL | 7 | 63 mL (630 mg) |
|  | B9 9% propofol | 1 mL | 8.0 mL | 9.0 mL | 7 | 63 mL (630 mg) |

Sample Collection and Preparation:

Serial blood samples (approximately 0.8 mL into $K_2$EDTA anticoagulant tube) were collected via a cephalic vein. Blood samples were collected at Predose (0 minute, only for study 2), 0.0333 (2 minutes), 0.0833 (5 minutes), 0.167 (10 minutes), 0.333 (20 minutes), 0.5 (30 minutes), 1, 2, 4, 6 and 8 hours post dose from all phases.

After collection, all blood samples were transferred into pre-labeled plastic micro-centrifuge tubes containing $K_2$EDTA (10 μL, 0.5 M) and placed on wet ice immediately upon collection. After blood was collected, the samples were processed for plasma by centrifugation at approximately 4° C., 3000 g for 10 minutes within 60 minutes of collection. The plasma was transferred into labeled polypropylene micro-centrifuge tubes and then quickly frozen over dry ice and stored frozen in a freezer set to maintain −60° C. or lower until bio-analysis.

Clinical Observation:

Cage-side observations for general health and appearance were done twice daily. Animals were given a physical examination prior to study initial to confirm animals' health. On dosing days, the animals were observed before and after each sample collection time point. General condition, behavior, activity, excretion, respiration or other unusual observations noted throughout the study were recorded.

Sample Analysis:

Dog plasma samples were analyzed for propofol using a qualified bioanalytical method based on protein precipitation followed by LC-MS/MS analysis. The lower limit of quantification (LLOQ) for propofol was 5.00 ng/mL or 10.0 ng/mL and the upper limit of quantification (ULOQ) was 2000 ng/mL.

Plasma concentration data of propofol was subjected to a non-compartmental pharmacokinetic analysis using a Phoenix WinNonlin software program (version 6.2.1, Pharsight, Mountain View, Calif.).

Terminal half-life ($T_{1/2}$), volume of distribution at steady state ($Vd_{ss}$), total body clearance (Cl), mean residence time (MRT) from time zero to the last quantifiable concentration ($MRT_{0-last}$) and from time zero to infinity ($MRT_{0-inf}$), the area under the plasma concentration-time curve (AUC) from time zero to the last quantifiable concentration ($AUC_{0-last}$) and AUC from time zero extrapolated to infinity ($AUC_{0-inf}$) were calculated using the linear/log trapezoidal rule.

Individual plasma concentrations below the lower limit of quantification (BQL) were excluded when performing pharmacokinetic analysis. Nominal sampling times were used to calculate all pharmacokinetic parameters. For samples collected within the first hour of dosing, a ±1 minute was acceptable; for the remaining time points, samples that were taken within 5% of the scheduled time were acceptable and were not considered as protocol deviation.

Figure 7A:
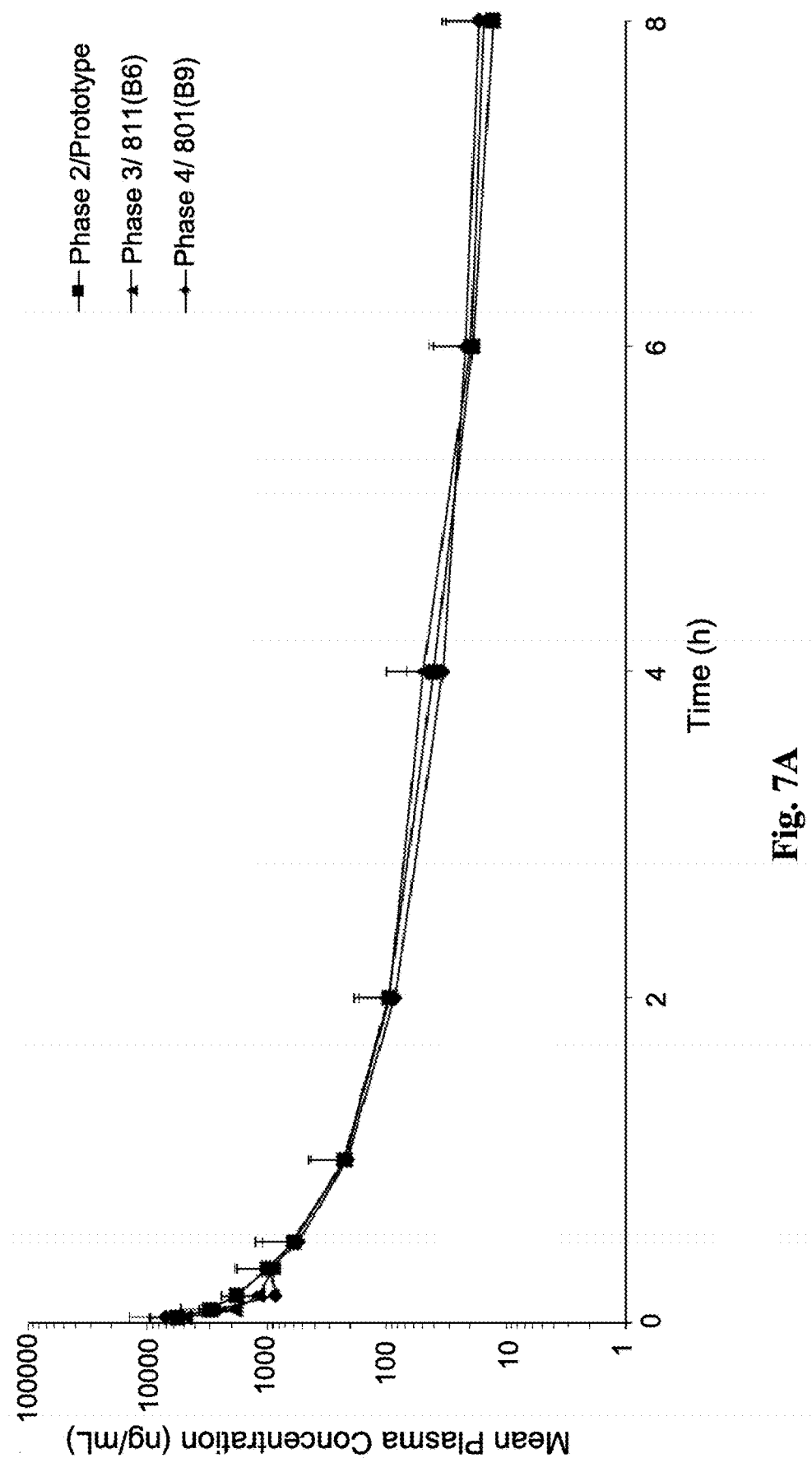
FIG. 7A shows the mean plasma concentration of propofol in study 1 following single intravenous Bolus administration, with formulations at a concentration of 10 mg/ml Propofol, to three non-naive male beagle dogs of prototype commercial lipid emulsion (Propofol-® Lipuro), B6A and B9A microemulsions at 6 mg/kg.
Figure 7B:
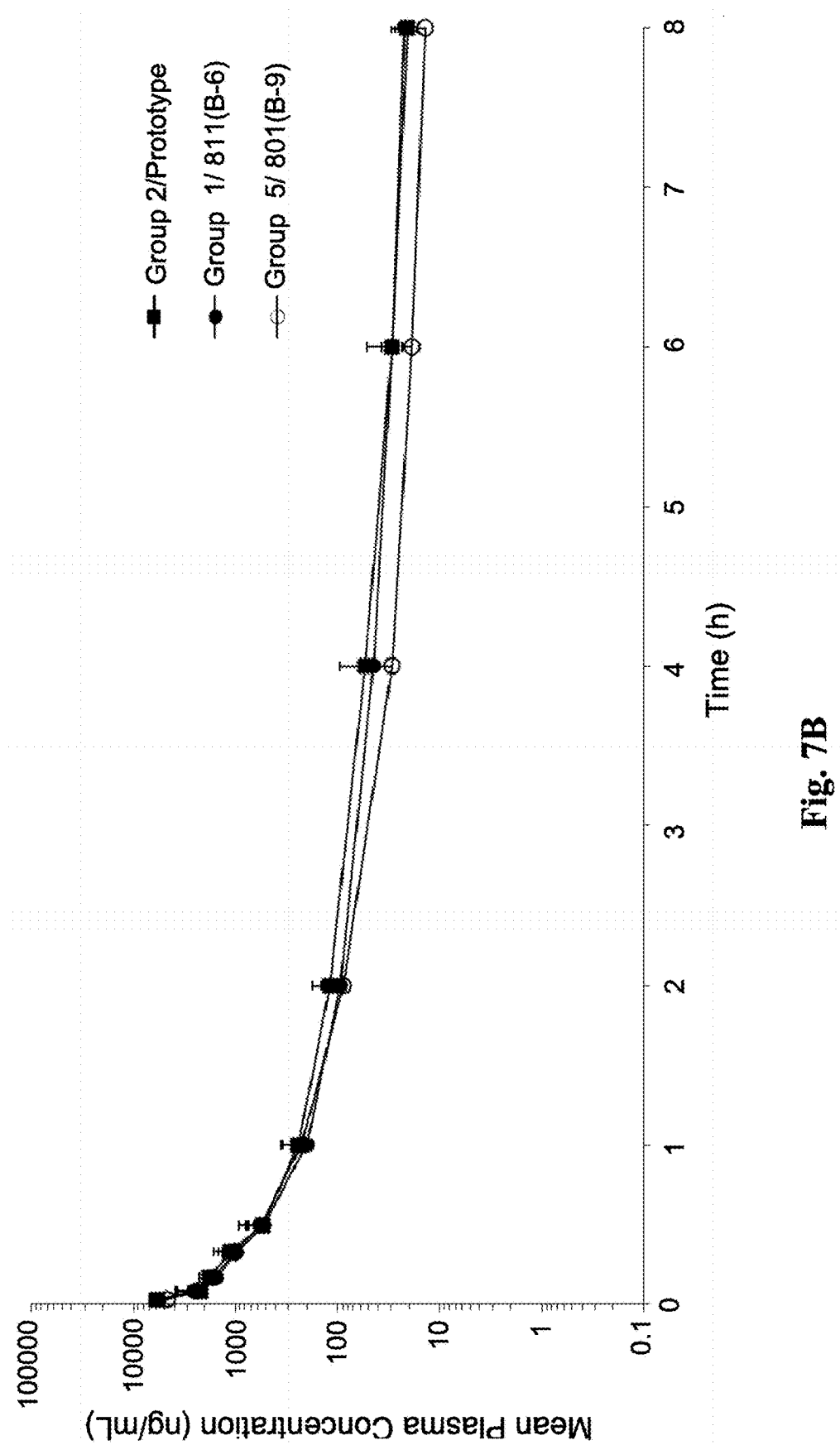
FIG. 7B shows the mean plasma concentration of propofol in study 2 following single intravenous Bolus administration of three formulations with a concentration of 10 mg/ml, to six naive male beagle dogs of: prototype commercial lipid emulsion (Propofol-® Lipuro), B6A and B9A formulation at 6 mg/kg.

Results:

Individual and Mean (n=3) plasma concentrations of propofol are presented graphically in FIGS. 7A-7B. The mean $C_0$, $T_{1/2}$, $V_{dss}$, Cl, $AUC_{0-last}$, $AUC_{0-inf}$, $MRT_{0-last}$ and $MRT_{0-inf}$ values of propofol after single intravenous dosing are provided in Table 13-3.

TABLE 13-3

Mean pharmacokinetic values after single intravenous dosing

| | Study # | | | | | |
|---|---|---|---|---|---|---|
| | 1 | | | 2 | | |
| | Phase | | | | | |
| | 2 | 3 | 4 | 2 | 1 | 5 |
| Formulation | Prototype | B6A* | B9A** | Prototype | B6A* | B9A** |
| $C_0$ (ng/mL) | 8867 | 9030 | 9223 | 12008 | 9400 | 7532 |

TABLE 13-3-continued

Mean pharmacokinetic values after single intravenous dosing

| | Study # | | | | | |
|---|---|---|---|---|---|---|
| | 1 | | | 2 | | |
| | Phase | | | | | |
| | 2 | 3 | 4 | 2 | 1 | 5 |
| $T_{1/2}$ (h) | 2.19 | 2.03 | 3.74 | 3.48 | 3.60 | 3.00 |
| $Vd_{ss}$ (L/kg) | 4.67 | 5.76 | 8.40 | 6.41 | 7.22 | 5.37 |
| Cl (ml/min/kg) | 67.1 | 70.7 | 74.6 | 58.0 | 63.2 | 70.5 |
| $AUC_{0-last}$ (ng · h/ml) | 1560 | 1377 | 1267 | 1660 | 1495 | 1384 |
| $AUC_{0-inf}$ (ng · h/ml) | 1600 | 1423 | 1360 | 1773 | 1607 | 1446 |
| $MRT_{0-last}$ (h) | 0.88 | 1.04 | 1.02 | 1.03 | 1.04 | 0.822 |
| $MRT_{0-inf}$ (h) | 1.15 | 1.36 | 1.87 | 1.92 | 1.90 | 1.30 |
| $AUC_{0-last}/AUC_{0-inf}$ (%) | 103 | 103 | 107 | 107 | 107 | 104 |

*designated in FIGS. 7A-7B as 811(B6)
**designated in FIGS. 7A-7B as 801(B9)

Study 1:

following Prototype administration to the 3 non-naive males beagle dogs, $C_0$ (initial plasma concentration) value (mean±S.D.) was observed at 8867±2844 ng/mL, $AUC_{0-inf}$ (the area under the concentration vs. time curve from time zero to the infinity) value (mean±S.D.) was obtained at 1600±541 ng/mL·hr and Cl (total body clearance) value (mean±S.D.) was obtained at 67.1±20.7 mL/min/kg.

Following 811(B6) administration to the 3 non-naive males beagle dogs, $C_0$ value (mean±S.D.) was observed at 9030±2080 ng/mL, $AUC_{0-inf}$ value (mean±S.D.) was obtained at 1423±136 ng/mL·hr and Cl value (mean±S.D.) was obtained at 70.7±7.03 mL/min/kg. The $C_0$, $AUC_{0-inf}$ and Cl values were comparable with those derived from commercial product Prototype dosing at the same dosage with the ratios of 1.02, 0.889 and 1.05, respectively. In terms of pharmacodynamics, all of the dogs fell into the state of anesthesia upon completing of the injection that lasted for 8 to 13 minutes without any adverse effects observed.

Following 801(B9) administration to the 3 non-naive male beagle dogs, $C_0$ value (mean±S.D.) was observed at 9223±5071 ng/mL, $AUC_{0-inf}$ value (mean±S.D.) was obtained at 1360±190 ng/mL·hr and Cl value (mean±S.D.) was obtained at 74.6±10.6 mL/min/kg. $C_0$, $AUC_{0-inf}$ and Cl values were comparable with those derived from commercial product Prototype dosing at the same dosage with the ratios of 1.04, 0.850 and 1.11, respectively. In terms of pharmacodynamics, all of the dogs fell into the state of anesthesia upon completing of the injection that lasted for 8 to 10 minutes without any adverse effects observed.

Study 2:

following Prototype (Propofol commercial emulsion) administration to the 6 naïve male beagle dogs, $C_0$ value (mean±S.D.) was observed at 12008±5932 ng/mL, $AUC_{0-inf}$ value (mean±S.D.) was obtained at 1773±324 ng/mL·hr and Cl value (mean±S.D.) was obtained at 58.0±10.7 mL/min/kg. The pharmacodynamics showed that all of the 6 dogs fell into the state of anesthesia smoothly at the end of injection and the anesthesia status lasted for about 5 to 7 min with mild degree of adverse effects such as swimming stroking limbs observed in 1 of the 6 dogs (D203).

Following 811(B6) administration to the 6 naive male beagle dogs, $C_0$ value (mean±S.D.) was observed at 9400±2572 ng/mL, $AUC_{0-inf}$ value (mean±S.D.) was obtained at 1607±219 ng/mL·hr and Cl value (mean±S.D.) was obtained at 63.2±8.17 mL/min/kg. $AUC_{0-inf}$ and Cl values were comparable with those derived for Prototype with the ratios of 0.906 and 1.09 respectively. The ratio of $C_0$ in 811(B6) to Prototype was 0.783, a bit lower than that of Prototype. All of the dogs fell into the state of anesthesia smoothly at about 20 seconds upon injection and the anesthesia status lasted for 10 to 11 minutes.

Following 801(B9) administration to the 5 naive male beagle dogs, $C_0$ value (mean±S.D.) was observed at 7532±749 ng/mL, $AUC_{0-inf}$ value (mean±S.D.) was obtained at 1446±218 ng/mL·hr and Cl value (mean±S.D.) was obtained at 70.5±11.8 mL/min/kg. $AUC_{0-inf}$ and Cl value was comparable with that derived from Prototype with the ratio to Prototype 0.816 and 1.22, while $C_0$ was lower than that of Prototype with a ratio to Prototype 0.627. 2 out of the 6 dogs fell into the state of anesthesia upon completion of injection.

Example VIX: Toxicology

Toxicokinetics (TK) was assessed after once every-other-day intravenous (IV) bolus administration of diluted formulations 811 (B6) and 811 (B9), and the commercial emulsion Propofol-® Lipuro 1% (10 mg/mL) to male and female beagle dogs for 7 days.

Dosing:

18 (9/sex) male and female dogs were randomly assigned to 3 groups (3/sex/group, Groups 1, 2 and 3) Animals were administered once every other day by IV bolus with 1 wt % propofol microemulsions 811 (B6) and, 801 (B9) and Propofol-® Lipuro 1% emulsion (10 mg/mL) at 6 mg/kg for 7 days, respectively.

The following parameters were examined during the study: viability, clinical observations, body weight, food consumption, respiratory rate, ECG, heart rate, clinical pathology (hematology and serum chemistry), gross pathology and histopathology and toxicokinetics.

Blood Sampling, Plasma Preparation and Analysis:

On Day 1 and Day 5, blood samples (approximately 1 mL into $K_2EDTA$ anticoagulant tube) were collected from all study animals at 0 (predose), 0.0333, 0.0833, 0.167, 0.333, 0.5, 1, 4, 8, 12 and 24 hours postdose via the cephalic vein from all animals Blood samples were collected into appropriately labeled tubes, inverted several times to ensure mixing and placed on wet ice. Plasma was obtained within 2 hours of collection by centrifugation at 3200×g and 4° C. for 15 minutes. Plasma was transferred into uniquely labeled polypropylene tubes (Eppendorf), covered by aluminum foil and frozen in the upright position immediately over dry ice and stored in a freezer set to maintain −60° C. to −80° C. on dry ice until analysis.

Dog plasma samples were analyzed for propofol using a validated bioanalytical method based on protein precipitation followed by ultra-performance liquid chromatographic triple quadrupole mass spectrometric (UPLC-MS/MS) analysis. Using 30 μL aliquot of dog plasma, the lower limit of quantification (LLOQ) was 10.0 ng/mL, and the higher limit of quantification was 6000 ng/mL.

Plasma concentration vs. time profiles of propofol were analyzed using a non-compartmental model by a validated WinNonlin® program (Pharsight, Version 6.2.1). The initial plasma concentration ($C_0$) and the area under the plasma concentration vs. time curve (AUC) from time zero to 24 hours post dose ($AUC_{0-24}$ h) were calculated using the linear up/log down trapezoidal rule.

Plasma concentration below LLOQ (BLQ) was set to zero for toxicokinetic analysis, however, when more than half (>50%) of the individual values at a single time point are BLQ, mean values will be reported as BLQ. $AUC_{0-24}$ h and $C_0$ values were reported to 3 significant digits. $AUC_{0-24}$ h and $C_0$ ratios were reported to 2 significant digits.

Results:

Two formulations B6-based and B9-based microemulsions, and one commercial emulsion product (Propofol-® Lipuro 1% (10 mg/mL)) administered by intravenous (IV) bolus to Beagle dogs once every other day (QOD) at 6 mg/kg dose level for a 7-day study period was well tolerated and all animals survived to the end of study. The mean±SD for $C_0$ and $AUC_{0-24\ h}$ values for propofol are presented in Table 14.

TABLE 14

Mean toxicokinetic values

| Group | Study day | Sex | $C_0$ (ng/mL) | $AUC_{0-24\ h}$ (h · ng/mL) |
|---|---|---|---|---|
| 1 | 1 | Male | 4560 ± 1740 | 1170 ± 133 |
|  |  | Female | 12800 ± 9260 | 1660 ± 478 |
|  | 5 | Male | 10700 ± 1720 | 1790 ± 239 |
|  |  | Female | 23600 ± 21800 | 3020 ± 2430 |
| 2 | 1 | Male | 14800 ± 540 | 1580 ± 117 |
|  |  | Female | 10800 ± 5350 | 1640 ± 326 |
|  | 5 | Male | 14100 ± 3630 | 1890 ± 413 |
|  |  | Female | 9120 ± 5870 | 1830 ± 668 |
| 3 | 1 | Male | 7630 ± 3080 | 1180 ± 290 |
|  |  | Female | 10700 ± 6760 | 1180 ± 462 |
|  | 5 | Male | 9500 ± 5580 | 1420 ± 358 |
|  |  | Female | 8810 ± 4470 | 1290 ± 456 |

Tested article related clinical signs such as slight skin redness discolored and swelling of the ears were observed only after the third day of administration. These clinical signs were reversible after few hours and noted.

There were no test article-related abnormal changes noted in body weight, food consumption, respiratory rate, ECG, heart rate and clinical pathology. Gross necropsy and organ weight findings were considered as not treatment related changes according to the histopathology evaluations.

No marked sex difference in systemic exposure was observed. No marked drug accumulation was observed.

The histopathology evaluations found no differences between the 2 tested formulations and the commercial emulsion groups. No treatment related changes were noted. A range of histopathological findings were noted in different organs, all are considered as incidental findings, characteristic for Beagle dogs of the same age. Injection site lesions were seen in some animals from all groups, consisting of focal or multifocal arterial wall hemorrhage, subchronic inflammation and endothelial hyperplasia, as well as periarterial subchronic inflammation. All these changes are considered to be related to needle trauma, and are not suggestive of potential local irritation, because of the sporadic incidence among the animals.

In conclusion, no obvious and clear difference was noted between the two tested formulations (B6 and B9 propofol-microemulsions) and the commercial lipid propofol emulsions, indicating the safety (lack of adverse effects) of the tested propofol-microemulsions.

Example VIIX: Pain Upon Administration Assessment

Pain and local irritation are known side-effects during administration of commercial propofol formulations. As noted above, the unique interaction between Solutol and propofol in formulations of the invention maintains propofol bound within the oil core of the microemulsion until sufficiently diluted within the bloodstream, enabling relatively pain-free administration of the formulation.

In order to assess the effectivity in formulating propofol into microemulsions of the invention with respect to administration-associated pain, a paw-licking test was carried out. B9A (1 wt % propofol) microemulsion was tested in comparison to Diprivan® (a commercially available injectable propofol emulsion) as positive control and 0.9% saline as negative control.

Forty-four Wealing male Sprague Dawley Rats were randomized to one of the four treatment groups (11 animals per group). The injected dose volume was titrated from 0.1 mL to 0.3 mL (corresponding to approximately 20 mg propofol/kg bodyweight) until the expected effect in the positive control group (Diprivan®) was observed. The first 4 animals in each dose group received 0.1 mL or 0.2 mL, and the data were not used for analysis in this study.

The total number of paw licks were recorded for 12 minutes, following sub-plantar injection. Total scores and means were compared using two-sample t-test. Scores were further evaluated in 2 subsets: Grade 1 (single paw lick episode) and Grade 2 (5 sec of uninterrupted licking).

No paw-licks were observed in the saline control animals. The mean combined score of rats injected with the positive control Diprivan®, had a total paw lick score of 14.7.

Animals treated with B9A displayed a mean combined score of 1.57 with no Grade 2 (5 sec of uninterrupted licking) observed. Statistically significant differences ($p \leq 0.05$) from the Diprivan® group were observed with respect to total mean licking scores and subset Grade 1 and 2 responses. The results are summarized in Table 15.

TABLE 15

Paw-lick scores - group totals

| Group |  | Grade 1 response | Grade 2 response | Combined score |
|---|---|---|---|---|
| Saline control | Total | 0 | 0 | 0 |
|  | Mean | 0 | 0 | 0 |
|  | SD | 0 | 0 | 0 |
| Diprivan ® | Total | 53 | 50 | 103 |
|  | Mean | 7.57 | 7.14 | 14.71 |
|  | SD | 4.76 | 8.49 | 4.90 |

TABLE 15-continued

Paw-lick scores - group totals

| Group | | Grade 1 response | Grade 2 response | Combined score |
|---|---|---|---|---|
| B9A | Total | 11 | 0 | 11 |
| | Mean | 1.57 | 0 | 1.57 |
| | SD | 2.15 | 0 | 0.81 |

One animal in the B9A group had a broken nail on the dosed paw which began bleeding. This likely contributed to the lick response. In case this animal would be excluded from the analysis, the number of licks in the B9A group would be as low as 5. Thus, the pain on injection observed with B9A was significantly lower than that observed with Diprivan®.

The invention claimed is:

1. A propofol-microemulsion comprising
an oil phase in the form of oil droplets dispersed in an aqueous diluent continuous phase, wherein the oil phase comprises propofol, at least one surfactant comprising polyethylene glycol 15-hydroxystearate (Solutol HS 15), at least one solvent comprising medium-chain triglycerides (MCT),
at least one co-surfactant, and
at least one co-solvent,
the oil droplets having a size of at most 20 nm in the continuous phase, the propofol and
the surfactant having diffusion coefficients having the same order of magnitude when in the microemulsion (as measured by SD-NMR), and the microemulsion being suitable for parenteral administration,
wherein the weight ratio between said at least one solvent and the surfactant is between about 1:8 and 1:12.

2. The propofol-microemulsion of claim 1, wherein the diffusion coefficients of propofol and the surfactant (when in the microemulsion) are at least of one order of magnitude smaller than the other components of the microemulsion.

3. The propofol-microemulsion of claim 1, wherein the diffusion coefficients of propofol and the surfactant (when in the microemulsion) are of an order of magnitude of $1\times10^{-11}$ $m^2$/sec, when in the microemulsion, as measured by SD-NMR.

4. The propofol-microemulsion of claim 1, wherein the polydispersity index (PDI) of the distribution of oil droplets is between about 0.03 and 0.08.

5. The propofol-microemulsion of claim 1, wherein the oil droplets size is between about 10 and 20 nm.

6. The propofol-microemulsion of claim 1, wherein said diluent is selected from water, water for injection, saline, dextrose solution, or a buffer having a pH between 3 and 9.

7. The propofol-microemulsion of claim 1, wherein the co-surfactant is different from said surfactant and is selected from polyols, diglycerides, polyoxyethylenes, lecithins and phospholipids, optionally wherein the co-surfactant is at least one polyol selected from ethylene glycol, glycerol, polyethylene glycol, polypropylene glycol, sorbitol, mannitol, lactitol and xylitol.

8. The propofol-microemulsion of claim 1, wherein the co-solvent is selected from ethanol, propanol, propylene glycol, and glycerol.

9. The propofol-microemulsion of claim 1, comprising propofol, Solutol HS 15, MCT, polyethylene glycol, propylene glycol, a co-solvent, and a diluent.

10. The propofol-microemulsion of claim 1, wherein the co-solvent is ethanol.

11. The propofol-microemulsion of claim 1, comprising between about 0.1 and 2 wt % propofol.

12. The propofol-microemulsion of claim 1, wherein (i) the weight ratio between propofol and the surfactant is between about 1:5 and 1:12, and/or (ii) the weight ratio between said at least one solvent and propofol is between about 1:2 and 1.25:1.

13. The propofol-microemulsion of claim 1, having one or more of the following characteristics: (i) being transparent, (ii) a turbidity value of between about 20 and 70 NTU, (iii) an osmolality value of between about 250 and 450 mOsm/Kg, (iv) a surface tension of between about 27 and 35 mN/m, and (v) being a Newtonian liquid.

14. A method of inducing an anesthetic effect to a subject in need thereof, comprising administering to the subject a propofol-microemulsion of claim 1.

15. A method for preventing irritancy or reducing pain during administration of propofol in a site of administration, the method comprising providing a propofol-microemulsion of claim 1 and administering said propofol-microemulsion to a patient in need thereof at a site of administration, the propofol being maintained within the oil droplets of the microemulsion during administration.

16. The propofol-microemulsion of claim 1, wherein the microemulsion has a mono-disperse size distribution of oil droplets.

17. A dilutable propofol-concentrate comprising propofol, at least one surfactant comprising polyethylene glycol 15-hydroxystearate (Solutol HS 15), at east one solvent comprising medium-chain triglycerides (MCT), at least one co-surfactant, and at east one co-solvent, wherein the weight ratio between said at east one solvent and the surfactant is between about 1:8 and 1:12.

18. A kit comprising means for holding a dilutable propofol-concentrate of claim 17 and at least one pharmaceutically acceptable aqueous diluent, and instructions of use.

19. The method of claim 18, wherein said diluent is water, saline, dextrose solution, or a buffer having a pH between 3 and 9.

20. A method for parenteral administration of propofol to a subject in need thereof, the method comprising diluting a dilutable propofol-concentrate of claim 17 to a predetermined effective amount in a pharmaceutically acceptable aqueous diluent, thereby obtaining a microemulsion suitable for parenteral administration, and administering said microemulsion parenterally to said subject.

21. The dilutable propofol-concentrate of claim 17, wherein the concentrate is free of water.

22. A process for preparing a composition suitable for parenteral administration of propofol, comprising diluting a dilutable propofol-concentrate of claim 17 in a predetermined quantity of a pharmaceutically acceptable aqueous diluent, optionally wherein said predetermined quantity of diluent is between about 75-98 wt %.

* * * * *